(12) United States Patent
Kotoda

(10) Patent No.: US 7,969,473 B2
(45) Date of Patent: Jun. 28, 2011

(54) IMAGE-PICKUP APPARATUS

(75) Inventor: Kaoru Kotoda, Tokyo (JP)

(73) Assignee: Olympus Corporation, Tokyo (JP)

(*) Notice: Subject to any disclaimer, the term of this patent is extended or adjusted under 35 U.S.C. 154(b) by 1142 days.

(21) Appl. No.: 11/700,250

(22) Filed: Jan. 31, 2007

(65) Prior Publication Data

US 2007/0183672 A1    Aug. 9, 2007

(30) Foreign Application Priority Data

Feb. 3, 2006 (JP) ................. 2006-026746

(51) Int. Cl.
H04N 5/232 (2006.01)
H04N 7/18 (2006.01)
A62B 1/04 (2006.01)

(52) U.S. Cl. ............... 348/211.3; 348/211.11; 348/159; 348/65

(58) Field of Classification Search ............ 348/218.1, 348/219.1, 211.3, 211.11, 65, 68, 143, 159, 348/46, 584, 211.4
See application file for complete search history.

(56) References Cited

U.S. PATENT DOCUMENTS

| 6,864,911 B1 * | 3/2005 | Zhang et al. ............... 348/211.1 |
| 7,106,361 B2 * | 9/2006 | Kanade et al. ................ 348/159 |
| 7,171,106 B2 * | 1/2007 | Elberbaum ................... 348/143 |
| 7,298,964 B2 * | 11/2007 | Ishikawa et al. ......... 348/211.11 |
| 2002/0109774 A1 * | 8/2002 | Meron et al. .................. 348/584 |
| 2004/0150724 A1 * | 8/2004 | Nozaki et al. ............... 348/211.4 |

FOREIGN PATENT DOCUMENTS

| JP | 1-174178 A | 7/1989 |
| JP | 2001-119722 | * 4/2001 |
| JP | 2001-119722 A | 4/2001 |
| JP | 2001-157197 A | 6/2001 |
| JP | 2002-262217 A | 9/2002 |
| JP | 2004-193683 A | 7/2004 |
| JP | 2005-503182 A | 2/2005 |
| JP | 2005-305180 A | 11/2005 |
| WO | WO 02/054932 A2 | 7/2002 |

OTHER PUBLICATIONS

Japanese Office Action dated Aug. 31, 2010, issued in corresponding Japanese Patent Application No. 2006-026746.

* cited by examiner

Primary Examiner — Nhan T Tran
(74) Attorney, Agent, or Firm — Westerman, Hattori, Daniels & Adrian, LLP

(57) ABSTRACT

Image-pickup sections and an image-communicating/processing section 138 are connected by a single bus. Following the output of the image data, an output-controlling section in one of the image-pickup sections outputs an image-data-ending pattern, which indicates the end of outputting the image data, to a bus. An ending-pattern-detecting section in another image-pickup section detects the image-data-ending pattern, and outputs an image-pickup-operation-starting signal. The another image-pickup section starts an image-pickup operation and output of the image data based on the image-pickup-operation-starting signal.

6 Claims, 22 Drawing Sheets

IMAGE-PICKUP APPARATUS

The present application is based on patent application No. 2006-026746 filed in Japan Feb. 3, 2006, the content of which is incorporated herein by reference.

BACKGROUND OF THE INVENTION

1. Field of the Invention

The present invention relates to an image-pickup apparatus used in, for instance, a monitoring camera or an endoscope that has a plurality of image-pickup sections, and more particularly to an image-pickup apparatus for processing and transmitting images, picked up by a plurality of image-pickup sections, by means of a single processing system and transmission path.

2. Description of Related Art

There is a demand that, a plurality of image-pickup sections be provided in one casing in monitoring cameras and endoscopes so as to pick up a wide perspective of images. For example, Published Japanese translation No. 2005-503182 of PCT International Publication proposes a system for obtaining a wide perspective image of human cavities. In this case, wide perspective images are picked up by an endoscope having a plurality of image-pickup sections corresponding to various optical paths, and images are transmitted outside of the human body from each image-pickup section.

Japanese Unexamined Patent Application, First Publication No. H1-174178 discloses a system having a single processing circuit, into which signals output from the plurality of image-pickup sections, are accumulated and output therefrom. FIG. 23 is a block diagram of the system. Picked-up images are output as image signals by image-pickup sections 2301 and 2302. Each image signal is input into an image-signal-switching circuit 2303. The image-signal-switching circuit 2303 switches two image signals by means of a control signal output from a pulse-producing mode controlling section 2305 and a switching timing signal output from a switching-pulse-producing circuit 2304, and puts them out to a signal-processing circuit 2306.

A synchronous-signal-producing circuit 2307 puts out a synchronization signal for operating each image-pickup section in a synchronized manner and various timing signals for producing processing times for operating a switching-pulse-producing circuit 2304 and a signal-processing circuit 2306. The signal-processing circuit 2306 performs predetermined process on the input image signal. The processed image signal is stored in a video tape recorder section 2308. Also, the stored image is output as an output image from the video tape recorder section 2308 to a display apparatus which is not shown in the drawing.

SUMMARY OF THE INVENTION

A first aspect in accordance with the present invention provides an image-pickup apparatus including: a plurality of image-pickup units including at least first and second image-pickup units each for picking up an image, producing and outputting image data; an image-processing unit for performing a predetermined data process on the image data; and a bus for connecting the first and second image-pickup units to the image-processing unit. In this aspect, the first image-pickup unit has an image-data-ending-pattern-outputting unit for outputting an image-data-ending pattern, which indicates the end of outputting the image data, to the bus, and the second image-pickup unit has an image-data-processing-ending-pattern-detecting unit for detecting the image-data-ending pattern output from the first image-pickup unit so that pick up of the image and output the image data start when the image-data-ending pattern is detected by the image-data-processing-ending-pattern-detecting unit.

Preferably, the first image-pickup unit further has an image-data-starting-pattern-outputting unit for outputting an image-data-starting pattern, which indicates the start of outputting the image data, to the bus, and the image-processing unit further has an image-data-starting-pattern-detecting unit for detecting the image-data-starting pattern output from the first image-pickup unit, so that the data process starts when the image-data-starting pattern is detected by the image-data-starting-pattern-detecting unit.

A second aspect in accordance with the present invention provides an image-pickup apparatus including: a plurality of image-pickup units including at least first and second image-pickup units each for picking up an image, and producing and outputting image data; an image-processing unit for performing a predetermined data process on the image data; and a bus for connecting the first and second image-pickup units to the image-processing unit. In this aspect, the first image-pickup unit further has an image-data-starting-pattern-outputting unit for outputting an image-data-starting pattern, which indicates the start of outputting the image data, to the bus, the image-processing unit further has: an image-data-starting-pattern-detecting unit for detecting the image-data-starting pattern output from the first image-pickup unit; and an image-processing-ending-pattern outputting unit for outputting the image-processing-ending pattern, which indicates the end of the data process, to the bus in synchronization with the timing of ending the data process, the second image-pickup unit further has the image-data-processing-ending-pattern-detecting unit for detecting the image-processing-ending pattern from the bus, the second image-pickup unit starts the pickup of an image and outputting of the image data when the image-processing-ending pattern is detected by the image-data-processing-ending-pattern-detecting unit, and the image-processing unit starts processing the image data when the image-data-starting pattern is detected by the image-data-starting-pattern-detecting unit.

Preferably, the image-processing unit further has a delay-information-adding unit for adding delay information, which relates to an interval between the end of data process and the start of pick up of an image, to the image-processing-ending pattern, and the second image-pickup unit further has a unit for controlling the timing of starting the picking up of an image, the unit controlling the timing of starting the pick up of an image based on the delay information added to the image-processing-ending pattern so that the pick up of the image starts after a lapse of time based on the delay information.

Preferably, the image-pickup apparatus further includes: a first lighting unit for lighting an object area picked up by the first image-pickup unit; and a second lighting unit for lighting an object area picked up by the second image-pickup unit. In this aspect, the first image-pickup unit further has: a first lighting-signal-producing unit for producing a first lighting signal for driving the first lighting unit; and a synchronous-lighting-pattern-outputting unit for outputting a synchronous lighting pattern onto the bus corresponding to the first lighting signal, and the second image-pickup unit further has: a synchronous-lighting-pattern-detecting unit for detecting the synchronous lighting pattern on the bus; and a second lighting-signal-producing unit for producing a second lighting signal for driving the second lighting unit when the synchronous lighting pattern is detected by the synchronous-lighting-pattern-detecting unit.

Preferably, the first image-pickup unit further has: an initial-setting-starting-pattern-outputting unit for outputting an initial-setting starting pattern, which indicates the start of outputting an initial-setting data, to the bus; and an initial-setting-data-outputting unit for outputting the initial-setting data to the bus after outputting the initial-setting-starting pattern. In addition, the second image-pickup unit further has: an initial-setting-data-storing unit for storing the initial-setting data; an initial-setting-starting-pattern-detecting unit for detecting the initial-setting-starting pattern on the bus; and an initial-setting-data-receiving unit for receiving the initial-setting data on the bus when the initial-setting-starting pattern is detected by the initial-setting-starting-pattern-detecting unit, the initial-setting-data-receiving unit storing the received initial-setting data in the initial-setting-data-storing unit.

Preferably, the second image-pickup unit further has: an initial-setting-starting-pattern-outputting unit for outputting a initial-setting starting pattern, which indicates the start of outputting initial-setting data, to the bus, the initial-setting data relating to a setting of operation modes of the first image-pickup unit; and an initial-setting-data-outputting unit for outputting the initial-setting data to the bus after outputting the initial-setting-starting pattern, and the first image-pickup unit further has: an initial-setting-data-storing unit for storing the initial-setting data; an initial-setting-starting-pattern-detecting unit for detecting the initial-setting-starting pattern on the bus; and an initial-setting-data-receiving unit for receiving the initial-setting data on the bus wherein the initial-setting-starting pattern is detected by the initial-setting-starting-pattern-detecting unit, the initial-setting-data-receiving unit storing the received initial-setting data in the initial-setting-data-storing unit.

DETAILED DESCRIPTION OF THE INVENTION

Figure 2:
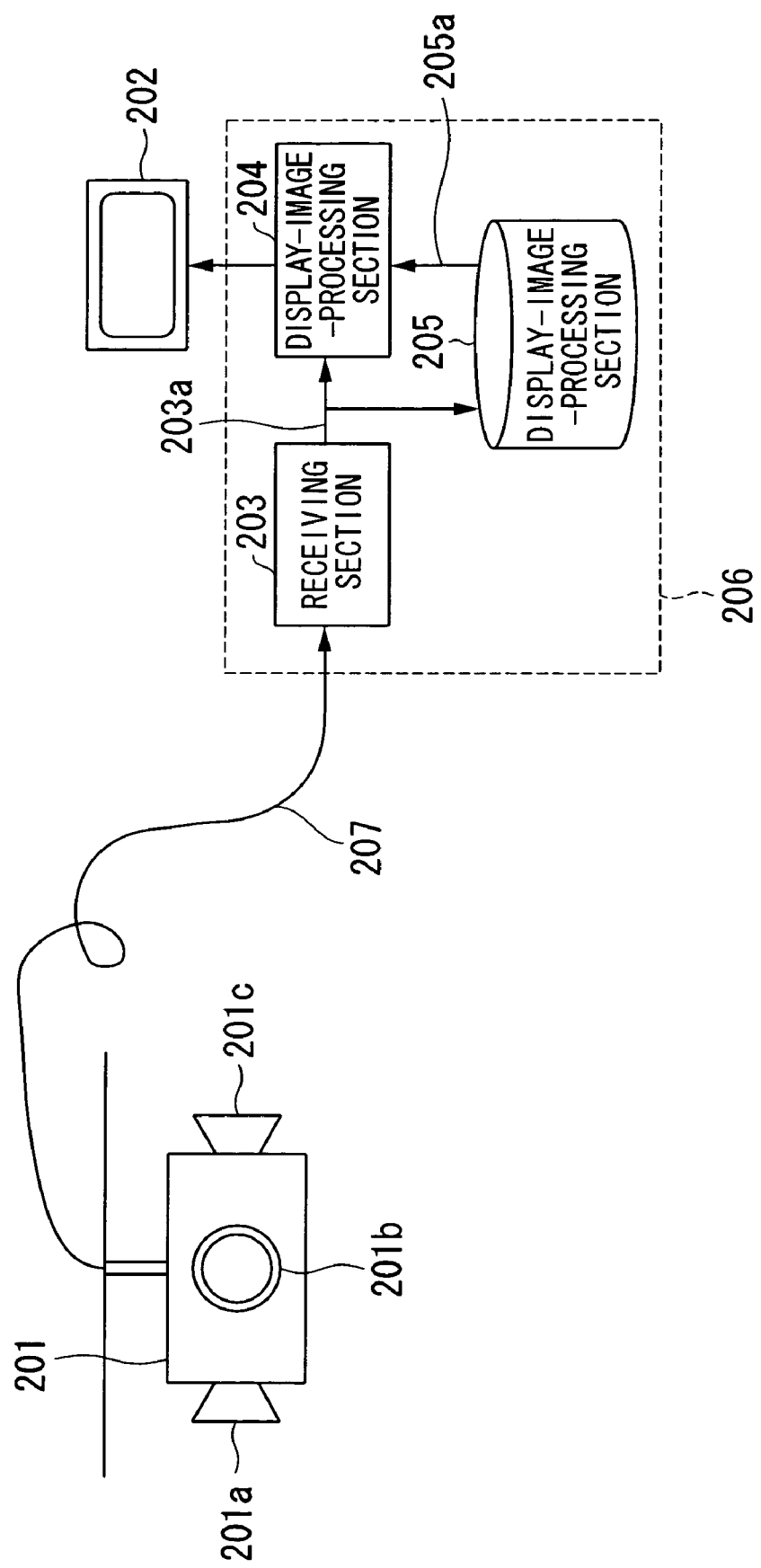
FIG. 2 is a schematic view of a monitoring camera system according to the first embodiment of the present invention.

Embodiments of the present invention will be explained below with reference to the drawings. To begin with, a first embodiment of the present invention will be explained. FIG. 2 illustrates the general configuration of a monitoring camera system using an image-pickup apparatus according to the present invention. Generally, monitoring camera systems should be able to cover a wide range of object areas. Considering this point, an image-pickup/communicating device 201 of a monitoring camera according to the present embodiment has three image-pickup sections 201a to 201c each picking up different object areas. Picked up images are transmitted, via a wired transmission path 207, to an image-displaying/accumulating device 206 provided in monitoring rooms, etc. A receiving section 203 receives image data in the image-displaying/accumulating device 206. The received images (received image 203a) are stored in an image-accumulating section 205 and input into a displayed-image-processing section 204. After various processes are conducted on the images (received image 203a or accumulated image 205a) in the displayed-image-processing section 204, an image is displayed on a monitor 202.

Figure 3:
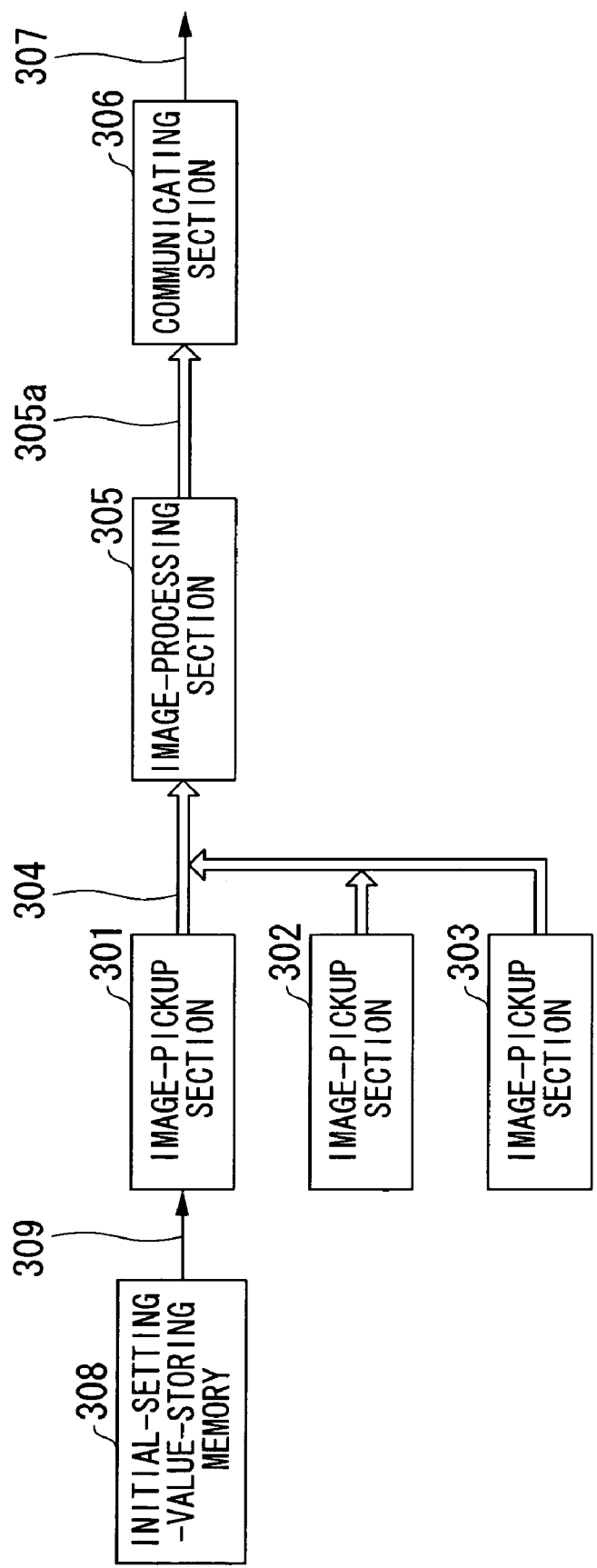
FIG. 3 is a block diagram of an image pickup/communication device of the monitoring camera according to the first embodiment of the present invention.

FIG. 3 shows the configuration of the image-pickup/communicating device 201 of the monitoring camera shown in FIG. 2. Image-pickup sections 301 to 303, each corresponding to the image-pickup sections 201a to 201c shown in FIG. 2, are connected to an image-processing section 305 via a bus 304. Since, eventually, there is one transmission path, each image-pickup section picks up an image, i.e., reading out an image signal from an optical sensor in an image-pickup element, sequentially using a time-division method. The input time-division image is processed, e.g., gamma compensation and white-balance compensation, in the image-processing section 305. The data 305a processed by the image-processing section 305 is input into a communicating section 306.

The communicating section 306 converts the input processed data 305a into a data having a format suitable for communication. That is, the communicating section 306 adds a redundancy code, converts into an electric signal, e.g., an low voltage differential signaling (LVDS) suitable for the transmission path, and outputs the data to a transmission path 307 (corresponding to the transmission path 207 shown in FIG. 2). An initial-setting-value-storing memory 308 stores an initial-setting value such as data-output format and an object area to-be-picked-up with respect to each image-pickup section. The initial-setting is retrieved from the initial-setting-value-storing memory 308 via an I2C bus 309, and is written into a setting-register in each image-pickup section via the bus 304 as described later.

Figure 4:
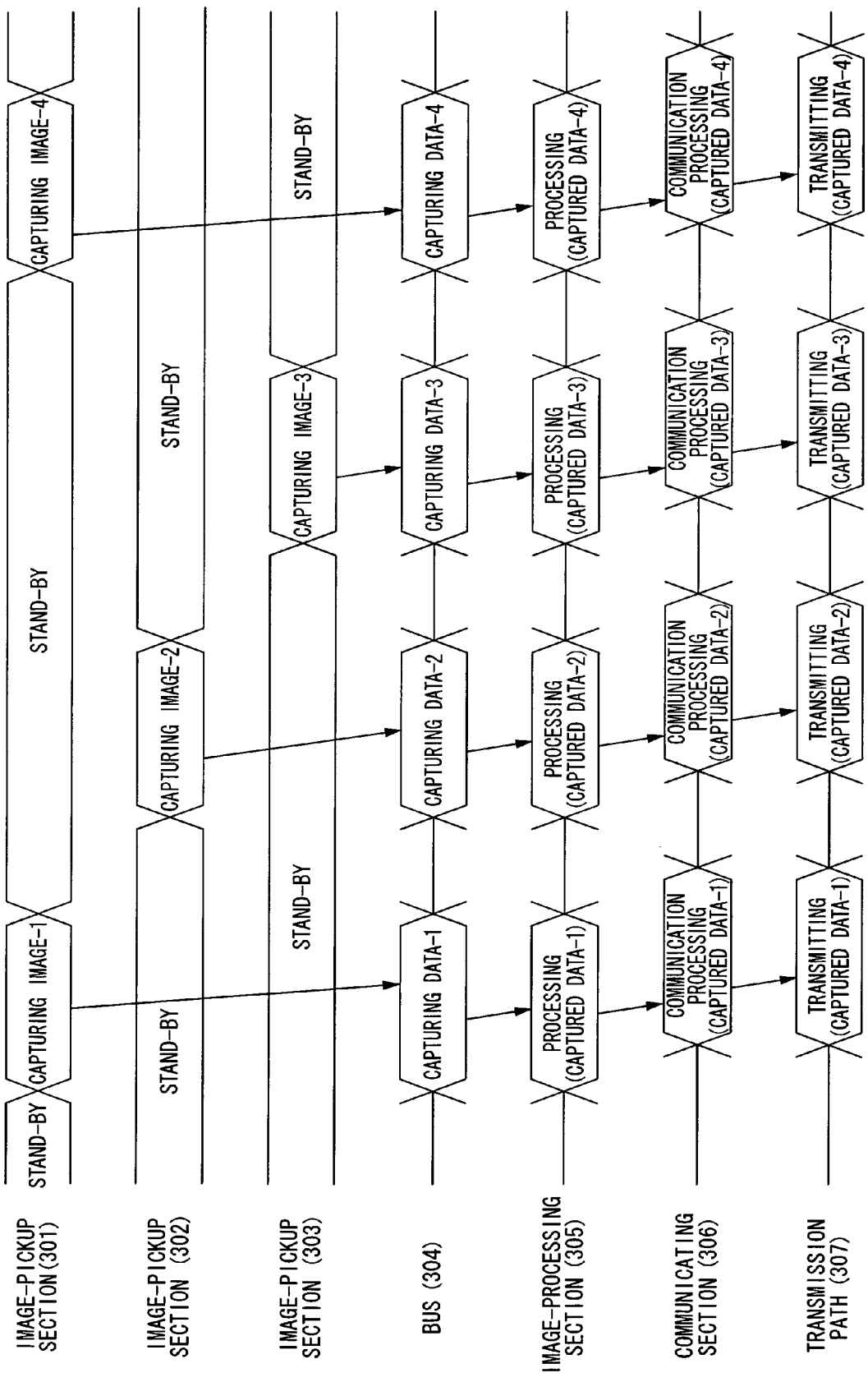
FIG. 4 is a timing diagram showing the operations of the entire image pickup/communication device of the monitoring camera according to the first embodiment of the present invention.

FIG. 4 is a timing diagram showing the approximate operation timing of the entire image-pickup/communicating device 201 of a monitoring camera. As shown in the timing diagram, the image-pickup sections 301 to 303 each pick up an image sequentially. Also, the image-pickup section 301 picks up an image (pick-up image-1) and outputs the picked-up data-1 in a digitized bayer format onto the bus 304. The picked-up data is input into an image-processing section 305. The image-processing section 305 compensates the picked-up data by means of image processing, e.g., Gamma compensation and white balance adjustment, and converts the data into, e.g., a YUV422 format data which can be easily processed afterward.

The data processed by the image-processing section 305 is output to the communicating section 306. With respect to the processed data, the communicating section 306 conducts an 8-10 conversion for communication use, adding a redundancy bit for correcting error in order to deal with noise in a communication, and outputs to the transmission path 307. After ending the operation in the image-pickup section 301, the image-pickup section 302 starts picking up an image in a way similar to the image-pickup section 301. Further, after ending the operation in the image-pickup section 302, the image-pickup section 303 starts picking up an image, and each image-pickup section operates sequentially.

As explained above, a wide range image is obtained since the image pickup/communication device of monitoring camera according to the present embodiment picks up an image by means of the plurality of image-pickup sections sequentially using a time-division method, processes the image, and transmits the processed image via one image-processing section and one transmission path.

Figure 1:
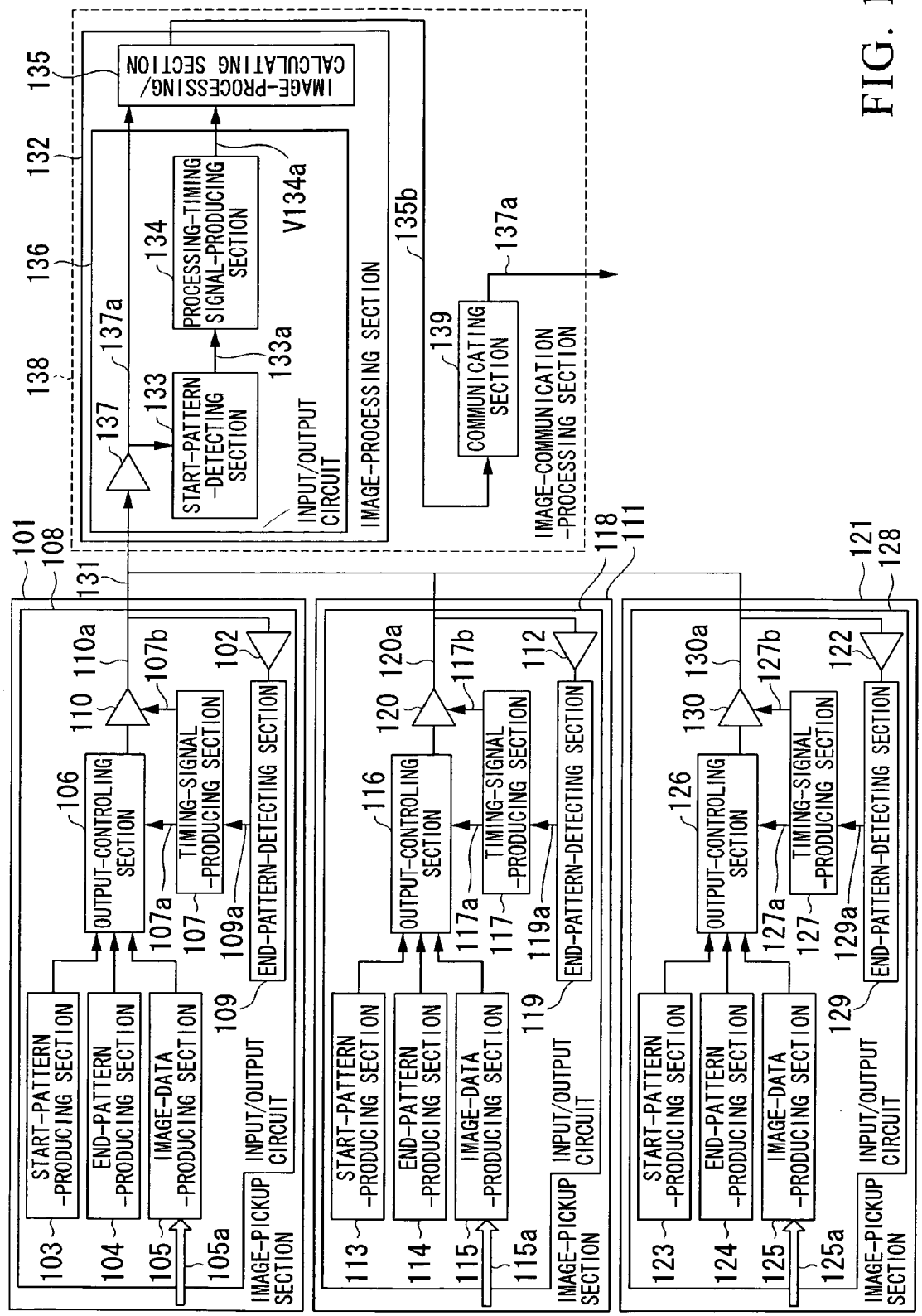
FIG. 1 is a block diagram showing the configurations of image-pickup sections and an image-processing section provided in an image pickup/communication device of a monitoring camera according to a first embodiment of the present invention.
Figure 5:
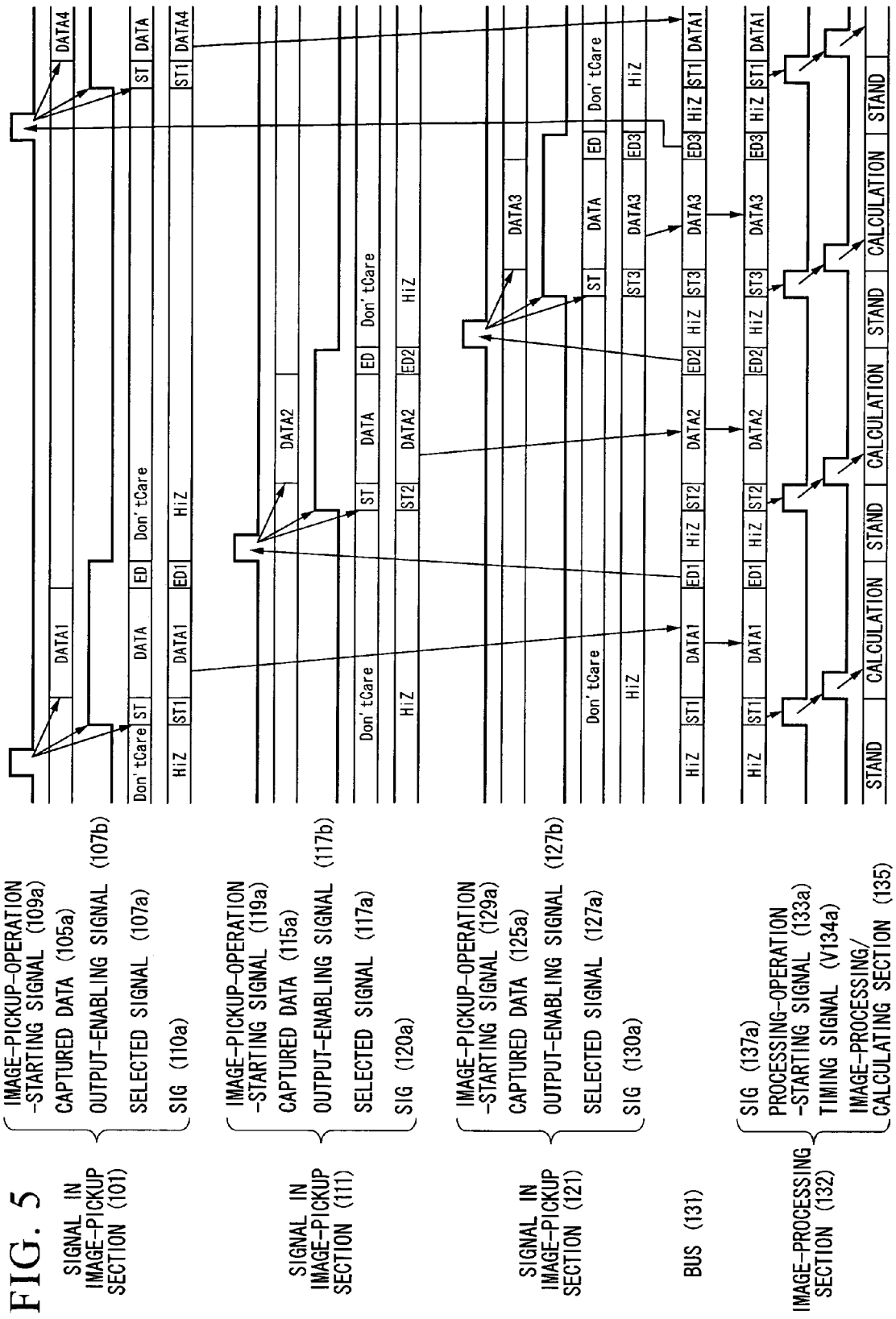
FIG. 5 is a timing diagram showing operations of the image-pickup sections and the image-processing section provided in the image pickup/communication device of monitoring camera according to a first embodiment of the present invention.

Next, details about the image-pickup sections and the image-processing section will be explained with reference to FIG. 1 showing configurations in each image-pickup section and the image-processing section and FIG. 5 showing a timing diagram with respect to the image-pickup section and the image-processing section. Image-pickup sections 101, 111, and 121 each shown in FIG. 1 correspond to the image-pickup sections 301, 302, and 303 shown in FIG. 3. The bus 131 corresponds to a bus 304 shown in FIG. 3. The image-processing section 132 shown in FIG. 1 corresponds to an image-processing section 305 shown in FIG. 3. The communicating section 139 shown in FIG. 1 corresponds to the communicating section 306 shown in FIG. 3. An image-processing section 132 and a communicating section 139 constitute an image-communicating/processing section 138. In the image-pickup sections, each one of input/output circuits 108, 118, and 128 has the same configuration as each other. Activation of the image-pickup-operation-starting signal (image-pickup-operation-starting signals 109a, 119a, and 129a shown in FIG. 1) starts the sequential operation of the image-pickup sections.

Operations in the image-pickup section 101 will be explained using signals in the image-pickup section 101 with reference to the timing diagram of FIG. 5. As shown in FIG. 5, when a image-pickup-operation-starting signal 109a becomes active, an output-enabling signal 107b for controlling an output to the bus 131 is activated, and the image-pickup section 101 starts outputting data to the bus 131 in the system. Firstly, the timing-signal-producing section 107 outputs an "ST", as a select signal 107a, which indicates selecting a starting pattern. Depending on the state of the select signal 107a, the output-controlling section 106 selects output from one of a starting-pattern producing section 103, an ending-pattern-producing section 104, and an image-data-producing section 105. When the "ST" is input as the select signal 107a, the output-controlling section 106 selects an output from the starting-pattern producing section 103 and outputs a starting pattern "ST1" as an SIG 110a, which indicates starting the output of data from the image-pickup section 101 to the bus 131 via the output-buffer 110.

Next, the timing-signal-producing section 107 outputs a "DATA" as a select signal 107a, which indicates selecting an output from the image-data-producing section 105. When the "DATA" is input as the select signal 107a, the output-controlling section 106 selects an output from the image-data-producing section 105 and outputs an image data "DATA1" as an SIG 110a to the bus 131 via the output-buffer 110. After outputting the image data, the timing-signal-producing section 107 outputs an "ED", as a select signal 107a, which indicates selecting an ending pattern. When the "ED" is input as a select signal 107a, the output-controlling section 106 selects output from the ending-pattern-producing section 104, and outputs an ending pattern "ED1" as an SIG 110a, which indicates an end of outputting data from the image-pickup section 101, to the bus 131 via the output-buffer 110.

With respect to outputting image data, sequential operations are conducted as explained above in the image-pickup section 101. As described previously, the image-pickup sections 101, 111, and 121 each conduct the same operations.

Next, sequential operations of picking up an image by means of the image-pickup sections 101, 111, and 121 will be explained. As described previously, the image-pickup section 101 sequentially outputs a starting pattern "ST1", an image data "DATA1", and an ending pattern "ED1" to the bus 131 based on the image-pickup-operation-starting signal 109*a* which is an inner signal of the image-pickup section 101. When the ending-pattern-detecting section 119 in the image-pickup section 111 detects the ending pattern "ED1" on the bus 131 via an input-buffer 112, the ending-pattern-detecting section 119 produces an image-pickup-operation-starting signal 119*a*. After that, as in the case of the image-pickup section 101, the image-pickup section 111 also starts the sequential operations based on the image-pickup-operation-starting signal 119*a*, and outputs a starting pattern "ST2", an image data "DATA2", and an ending pattern "ED2" to a bus 131.

Next, when an ending-pattern-detecting section 129 in an image-pickup section 121 detects the ending pattern "ED2" on the bus 131 via an input-buffer 122, the ending-pattern-detecting section 129 produces an image-pickup-operation-starting signal 129*a*.

As in the cases of the image-pickup sections 101 and 111, the image-pickup section 121 also starts the sequential operations based on the image-pickup-operation-starting signal 129*a*, and outputs a starting pattern "ST3", an image data "DATA3", and an ending pattern "ED3" to the bus 131. Further, when an ending-pattern-detecting section 109 in the image-pickup section 101 detects the ending pattern "ED3" on the bus 131 via an input-buffer 102, the ending-pattern-detecting section 109 produces an image-pickup-operation-starting signal 109*a*. Similarly, the image-pickup section 101 also starts the sequential operations based on the image-pickup-operation-starting signal 109*a*, and outputs a starting pattern "ST1", an image data "DATA4", and an ending pattern "ED1" to the bus 131.

As described above, sequential operations are conducted in each image-pickup section by detecting an ending pattern from a specific image-pickup section.

Next, operations in the image-processing section 132 will be explained. Starting patterns ("ST1", "ST2", "ST3", and "ST4") as SIGs 137*a*, each of which indicates the start of outputting data from each image-pickup section, are input into an input/output circuit 136 in the image-processing section 132 via an input-buffer 137. A starting-pattern-detecting section 133 detects these starting patterns, and outputs a processing-operation-starting-signal 133*a*. When the processing-operation-starting-signal 133*a* is input into a processing-timing-producing section 134, the processing-timing-producing section 134 produces a timing signal V134*a* for activating an image processing/calculating section 135. When an image data as an SIG 137*a* on the bus 131 is input into the image processing/calculating section 135, the image processing/calculating section 135 conducts data processes such as gamma compensation and white-balance adjustment, and outputs the resulting processed data 135*b* to a communicating section 139.

As described previously, the sequential operations are conducted in each image-pickup section and the image-processing section by detecting the starting pattern and the ending pattern corresponding to each image-pickup section from the bus. In this case, for instance, there is a possibility that ending patterns equivalent to each other existing in an image data cause a detection error, and thus, incorrect image data be erroneously output from these image-pickup sections. In a case that the image-pickup sections output a luminance-and-color-difference (YUV) data format, the above error detection is prevented by the configuration below.

In general, in luminance-and-color-difference (YUV) 8-bit image data, luminance signals use values ranging from 10 to 245, and color-difference signals use values indicated by upper and lower limits where the width of the limits is 235, i.e., typically 128. That is, a concurrence of equivalent patterns in one image data can be prevented by using values outside the range, i.e., 0 to 9 and 246 to 255 for image starting patterns and image-ending patterns. For instance, "255" (0xFF) may be used as a starting pattern, and "1" (0x01), "2" (0x02), and "3" (0x03) may be used as ending patterns corresponding to each image-pickup section.

That is, in this configuration, the ending-pattern-producing section 104 shown in FIG. 1 may output an ending pattern "1", the ending-pattern-producing section 114 may output an ending pattern "2", and the ending-pattern-producing section 124 may output an ending pattern "3". Also, in this configuration with respect to detecting ending patterns from each image-pickup section, the ending-pattern-detecting section 109 in the image-pickup section 101 detects the ending pattern "3", the ending-pattern-detecting section 119 in the image-pickup section 111 detects the ending pattern "1", and the ending-pattern-detecting section 129 in the image-pickup section 121 detects the ending pattern "2".

The above configuration can prevent the detection error attributable to equivalent patterns in image data. Although 20 patterns can be used in 8-bit format, more patterns may be produced by using a 2-byte (16-bit) format in which complex patterns are combined.

Figure 6:
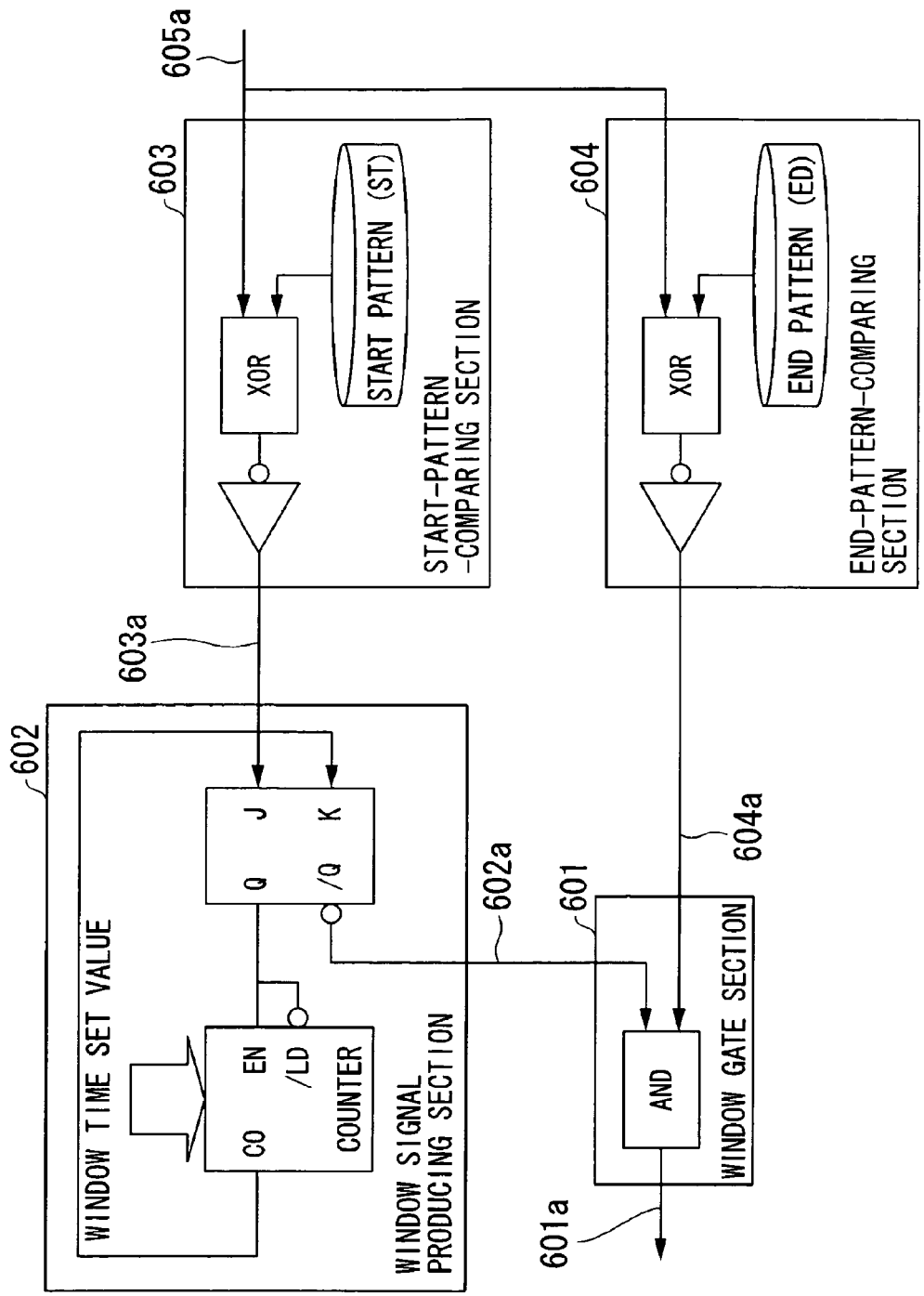
FIG. 6 is a block diagram showing the configuration of ending-pattern-detecting sections provided in the image pickup/communication device of the monitoring camera according to the first embodiment of the present invention.

RGB data format output from the image-pickup sections using values 0 to 255 may cause a detection error in the above explained starting and ending patterns. FIG. 6 shows a configuration of an ending-pattern-detecting section for preventing such a detection error. In FIG. 6, a starting-pattern-comparing section 603 compares a predetermined starting pattern with a predetermined bus data input 605*a*. An ending-pattern-comparing section 604 compares a predetermined ending pattern with the bus data input 605*a*. A window-signal-producing section 602 outputs a window signal 602*a* having a predetermined pulse duration based on a coinciding starting-pattern signal 603*a* output from the starting-pattern-comparing section 603. A window gate section 601 gates a coinciding-ending-pattern signal 604*a* by means of a window signal 602*a*.

Figure 7:
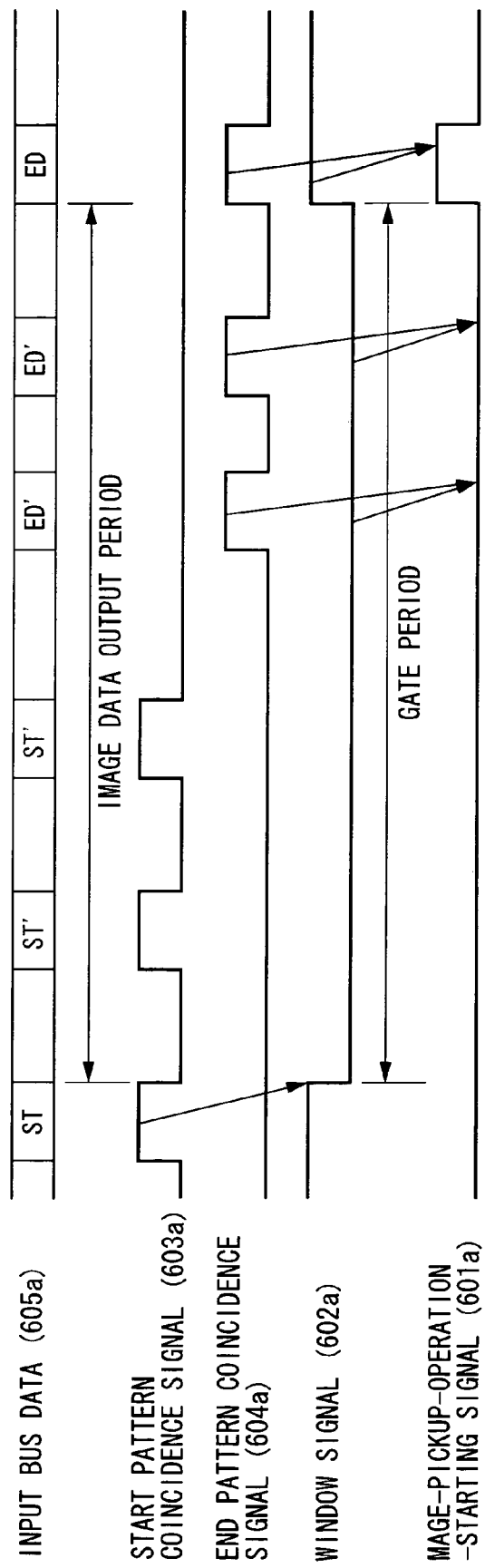
FIG. 7 is a timing diagram showing the operation timing of an ending-pattern-detecting section provided in the image pickup/communication device of the monitoring camera according to the first embodiment of the present invention.

Operations in the ending-pattern-detecting section will be explained with reference to a timing diagram shown in FIG. 7. As described previously, data equivalent to a starting pattern (described as "ST") and an ending pattern (described as "ED") are output onto a bus because values used in image data are arbitrary. "ST'" and "ED'" described in a row regarding a bus data input 605*a* in FIG. 7 is data (pseudo-patterns) equivalent to starting and ending patterns that will be added before and after image data.

The starting-pattern-comparing section 603 determines as to whether or not a value in the bus data input 605*a* coincides with a starting pattern (ST) by means of an exclusive OR circuit (XOR). A coinciding starting-pattern signal 603*a* is activated corresponding to the sections indicated as "ST" and the "ST'" in the row of bus data input 605*a*. Similarly, the ending-pattern-comparing section 604 determines as to whether or not a bus data input 605*a* coincides with an ending pattern. A coinciding-ending-pattern signal 604*a* is activated corresponding to the sections indicated as "ED" and the "ED'" in the row of bus data input 605*a*.

A window signal 602*a* persists for a certain prescribed period after a coinciding starting-pattern signal 603*a* is produced. When the coinciding starting-pattern signal 603*a* in the window-signal-producing section 602 shown in FIG. 6 becomes active, a counter thereinside begins incrementing, and the window signal 602*a* becomes inactive during a period defined as a window period, i.e., an image-data-output period. In the event that the window signal 602*a* is inactive, since the window gate section 601 gates the coinciding-ending-pattern signal 604*a*, all ending-pattern-coincidence signals 604*a* that are produced due to detecting a pseudo-ending-pattern "ED" in the image data are gated, so only the ending-pattern-coincidence signals 604*a* produced due to detecting true ending-pattern "ED" are output.

The ending-pattern-detecting section having the above explained configuration is operable properly, i.e., without detecting ending patterns erroneously. A starting pattern-detecting section in the image-processing section has similar configurations in which signals for starting process and operation are not output during a period equivalent to an image-data-output period.

Figure 8:
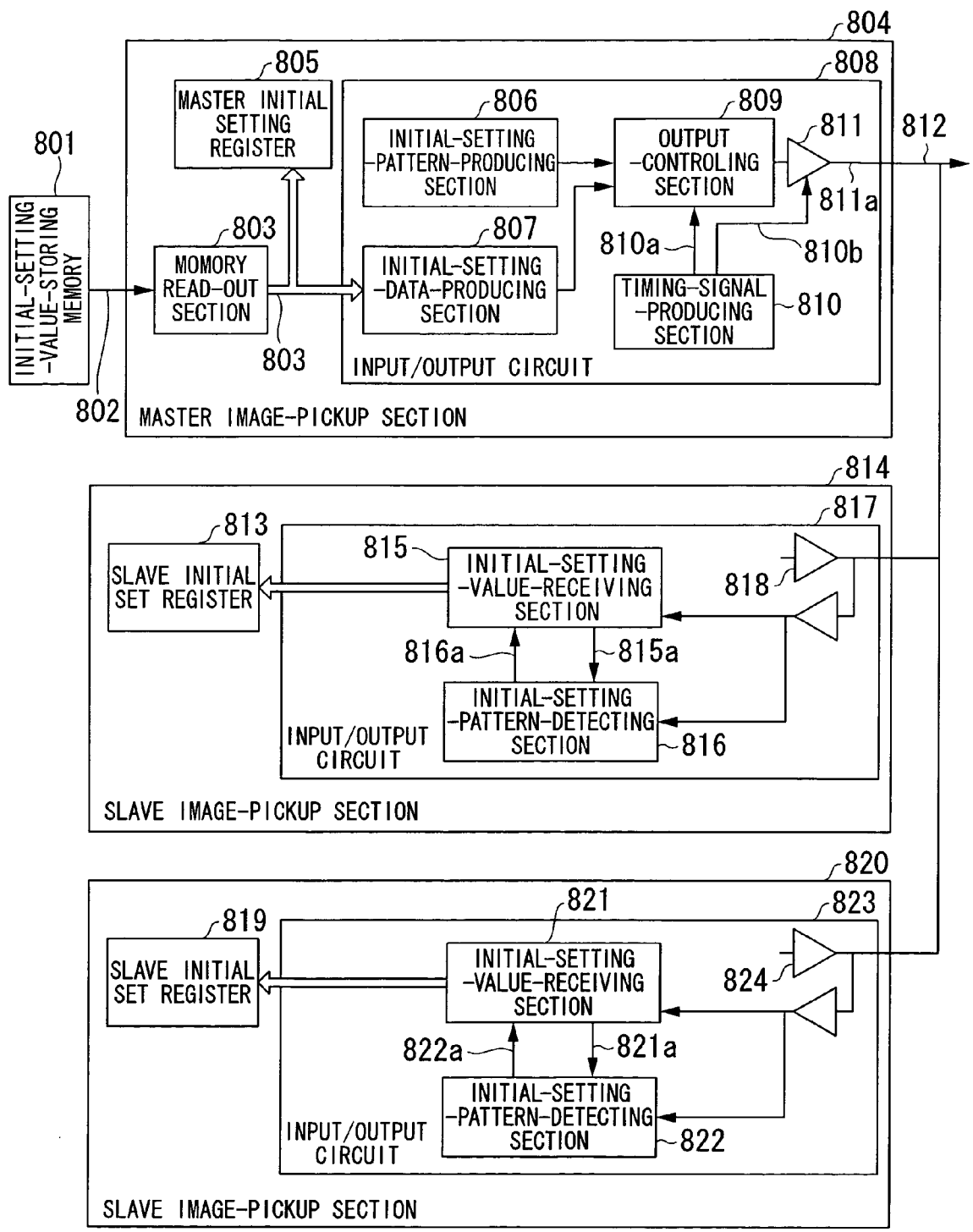
FIG. 8 is a block diagram showing the configuration based on an initial-setting of the image-pickup sections provided in the image pickup/communication device of the monitoring camera according to the first embodiment of the present invention.

Next, initial-setting operations of the image-pickup section according to the present embodiment will be explained. Generally, various modes, e.g., previously-described output data format (YUV, RGB), a frame rate, and an area-to-be-picked-up (number and position of pixel), are entered in a register of an image-pickup section. The modes are normally stored in non-volatile memory in a system, and the modes enter into the register of each image-pickup section from the non-volatile memory when the power is turned on. FIG. 8 shows the configuration of image-pickup sections based on initial-setting according to the present embodiment.

A master image-pickup-section 804 corresponds to the image-pickup section 101 shown in FIG. 1, and slave image-pickup sections 814 and 820 correspond to the image-pickup sections 111 and 121 shown in FIG. 1. An initial-setting-value-storing memory 801 (corresponding to an initial-setting-value-storing memory 308 shown in FIG. 3) stores values for setting all the image-pickup sections. The initial-setting-value-storing memory 801 is connected to the master image-pickup-section 804 via a serial bus 802 (corresponding to the I2C bus 309 shown in FIG. 3).

In the master image-pickup-section 804, the memory-retrieval section 803 retrieves the setting values from the initial-setting-value-storing memory 801. A master initial-setting register 805 stores the values retrieved by the memory-retrieval section 803. An initial-setting-data-producing section 807 outputs an initial-setting data, which indicates the setting values retrieved by the memory-retrieval section 803 to an output-controlling section 809 (corresponding to the output-controlling section 106 shown in FIG. 1). An initial-setting-pattern-producing section 806 produces an initial-setting pattern which indicates the start of the initial-setting data.

In the image-pickup section other than the master image-pickup-section 804, i.e., in the slave image-pickup sections 814 and 820, initial-setting-pattern-detecting sections 816 and 822 detect an initial-setting pattern on a bus 812 (corresponding to the bus 131 shown in FIG. 1). Initial-setting-value-receiving sections 815 and 821 receive an initial-setting data from the bus 812. Slave initial-setting registers 813 and 819 store the initial-setting values.

Components that are the same as the starting-pattern producing section 103, the ending-pattern-producing section 104, and the image-data-producing section 105 are connected to an output-controlling section 809 (corresponding to the output-controlling section 106 shown in FIG. 1). A component that is the same as the ending-pattern-detecting section 109 shown in FIG. 1 is connected to a timing-signal-producing section 810 (corresponding to the timing-signal-producing section 107 shown in FIG. 1) which is not shown in FIG. 8. Components that are the same as part of the components shown in FIG. 1 are omitted in the slave image-pickup sections 814 and 820. Also, outputting buffers 811, 818, and 824 each correspond to the output buffers 110, 120, 130 shown in FIG. 1.

Figure 9:
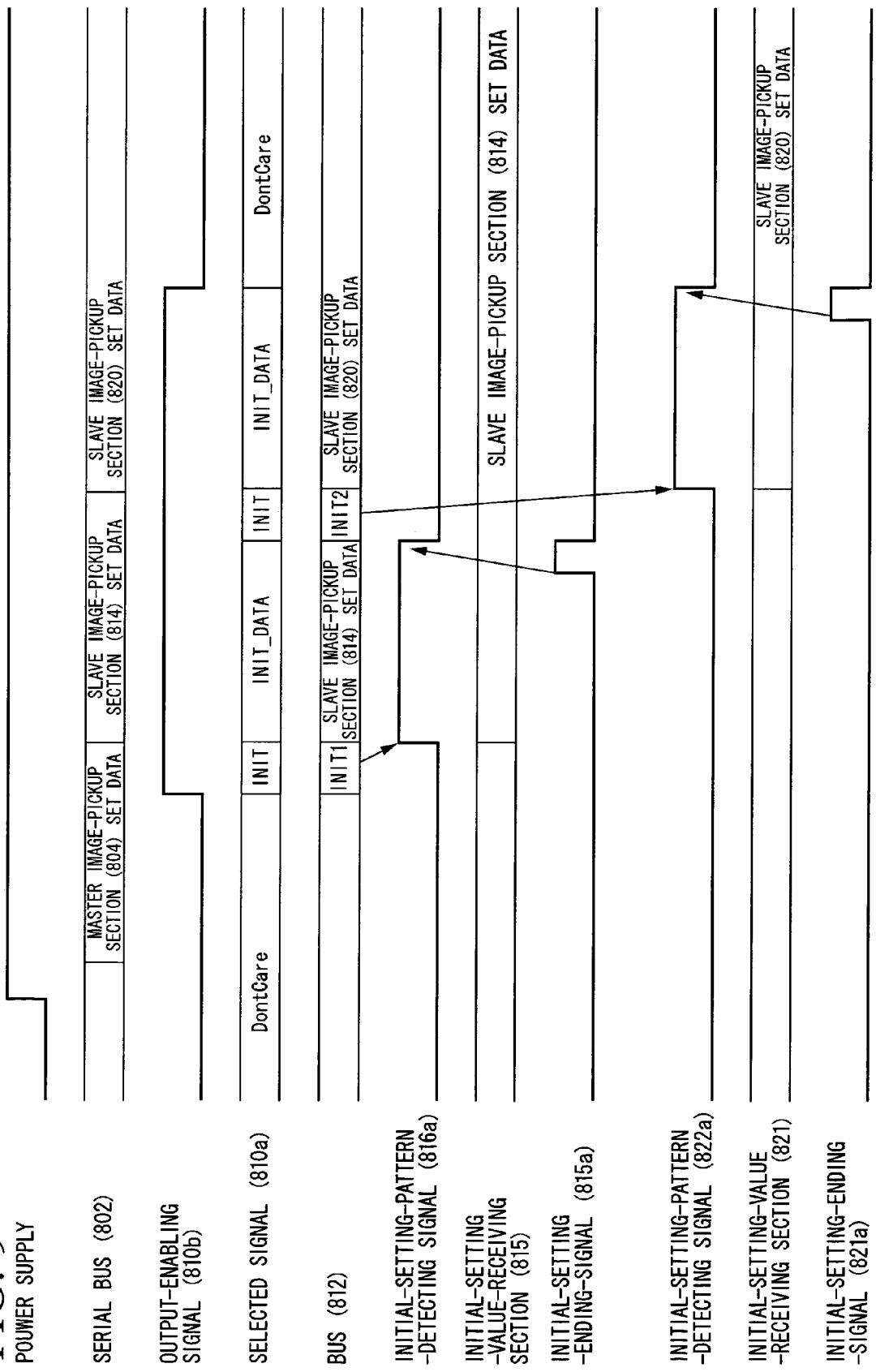
FIG. 9 is a timing diagram showing operation timing of the image-pickup sections, based on the initial-setting, provided in the image pickup/communication device of the monitoring camera according to a first embodiment of the present invention.

Next, operations concerning the initial-setting will be explained with reference to FIG. 8 and the timing diagram shown in FIG. 9. As shown in FIG. 9, after the power is turned on, the memory-retrieval section 803 in the master image-pickup-section 804 starts retrieving an initial-setting data (set value) from the initial-setting-value-storing memory 801 via the serial bus 802. The memory-retrieval section 803 retrieves the values to be set in the master image-pickup-section 804 first, and then stores them in the master initial-setting register 805.

Next, the memory-retrieval section 803 starts retrieving an initial-setting data to be set in the slave image-pickup section 814. The timing-signal-producing section 810 in the master image-pickup-section 804 activates an output-enabling signal 810*b*, and outputs an "INIT" as a selection signal 810*a* for selecting an initial-setting pattern which indicates the start of outputting an initial-setting value (initial-setting data) to the slave image-pickup section 814. When the "INIT" as the selection signal 810*a* is input into the output-controlling section 809, the output-controlling section 809 selects an output from the initial-setting-pattern-producing section 806, and outputs an "INI1", which indicates starting initial-setting data of the slave image-pickup section 814, to the bus 812 via the buffer 811. When an initial-setting-pattern-detecting section 816 in the slave image-pickup section 814 detects the "INI1", the initial-setting-pattern-detecting section 816 activates an initial-setting-pattern-detecting signal 816*a*. A timing-signal-producing section 810 in the master image-pickup-section 804 outputs an "INIT_DATA" for selecting an output of the initial-setting data as the selection signal 810*a*. When the "INIT_DATA" as the selection signal 810*a* is input into the output-controlling section 809, the output-controlling section 809 selects an output from the initial-setting-data-producing section 807, and outputs the initial-setting data to be set in the slave image-pickup section 814 to the bus 812.

When the initial-setting-pattern-detecting signal 816*a* becomes active in the slave image-pickup section 814, the initial-setting-value-receiving section 815 receives the initial-setting data on the bus 812, and stores the initial-setting data in the slave initial-setting register 813. After all the initial-setting values are stored, the initial-setting-value-receiving section 815 activates an initial-setting-completion signal 815*a*. The initial-setting-pattern-detecting signal 816*a* is released by the initial-setting-completion signal 815*a*; thus, the initial-setting of the slave image-pickup section 814 finishes.

Next, the timing-signal-producing section 810 in the master image-pickup-section 804 outputs an "INIT" as a selection signal 810*a* for selecting an initial-setting pattern, which indicates the start of newly outputting the initial-setting data to the slave image-pickup section 820. When the "INIT" as the selection signal 810*a* is input into the output-controlling section 809, the output-controlling section 809 selects an output from the initial-setting-pattern-producing section 806, and outputs an "IN12", which indicates the start of initial-setting data of the slave image-pickup section 820 to the bus 812. After that, the slave image-pickup section 820 conducts operations similar to those conducted in the slave image-pickup section 814.

According to the above described operations, an initial-setting value for each image-pickup section is retrieved from the initial-setting-value-storing memory 801 connected to the master image-pickup-section 804, and stored in a register in each image-pickup section. Thus, initial-setting values can be retrieved and set without connecting a memory storing initial-setting values to all the image-pickup sections directly. Although the master image-pickup-section 804 corresponds to the image-pickup section 101 shown in FIG. 1 in the above description, the present invention is not limited to such a configuration. The master image-pickup-section 804 can be any one of the image-pickup sections as long as the memory storing initial-setting values is connected thereto.

As described above, each image-pickup section is connected to a single bus in the image-pickup apparatus according to the present embodiment, and a specific ending pattern is output from the ending-pattern-producing section after the output of an image data is completed in each image-pickup section. Also, the ending-pattern-detecting section in each image-pickup section detects an ending pattern corresponding to a specific image-pickup section, and starts picking up an image. By doing this, each image-pickup section sequentially conduct an image-pickup operation exclusively, i.e., without providing a signal line for controlling the operation in each image-pickup section.

The initial-setting-pattern-producing section and the output-controlling section in the master image-pickup-section output the initial-setting pattern, corresponding to each slave image-pickup sections, to the bus prior to outputting of the initial-setting data. Following this, the initial-setting-data-producing section and the output-controlling section in the master image-pickup section output the initial-setting data to be set in the slave image-pickup sections. The initial-setting-pattern-detecting section in each slave image-pickup section detects the initial-setting pattern corresponding to each slave image-pickup section, and outputs an initial-setting-pattern-detecting signal. The initial-setting-value-receiving section receives data on the bus as the initial-setting data based on the initial-setting-pattern-detecting signal, and stores the received data in the initial-setting register thereinside. By doing this, initial-setting values can be set in each image-pickup section without providing a signal line for controlling the operation in each image-pickup section.

Therefore, according to the present embodiment, the number of signal lines which connect each image-pickup section to the image-processing section can be reduced, and a simple circuit configuration can be obtained more easily. Also, since each image-pickup section and the image-processing section are connected by a bus so that a selecting circuit inserted among the plurality of image-pickup sections and the image-processing section or additional wirings used for transmitting control signals are not necessary, the initial-setting of each image-pickup section and image data transmission can be conducted while preventing competitions for the bus. The simple circuit configuration provides a small image-pickup apparatus as well. Although the present embodiment provides an example using three image-pickup sections, different number of similarly-configured image-pickups can be realized in the present invention.

Figure 10:
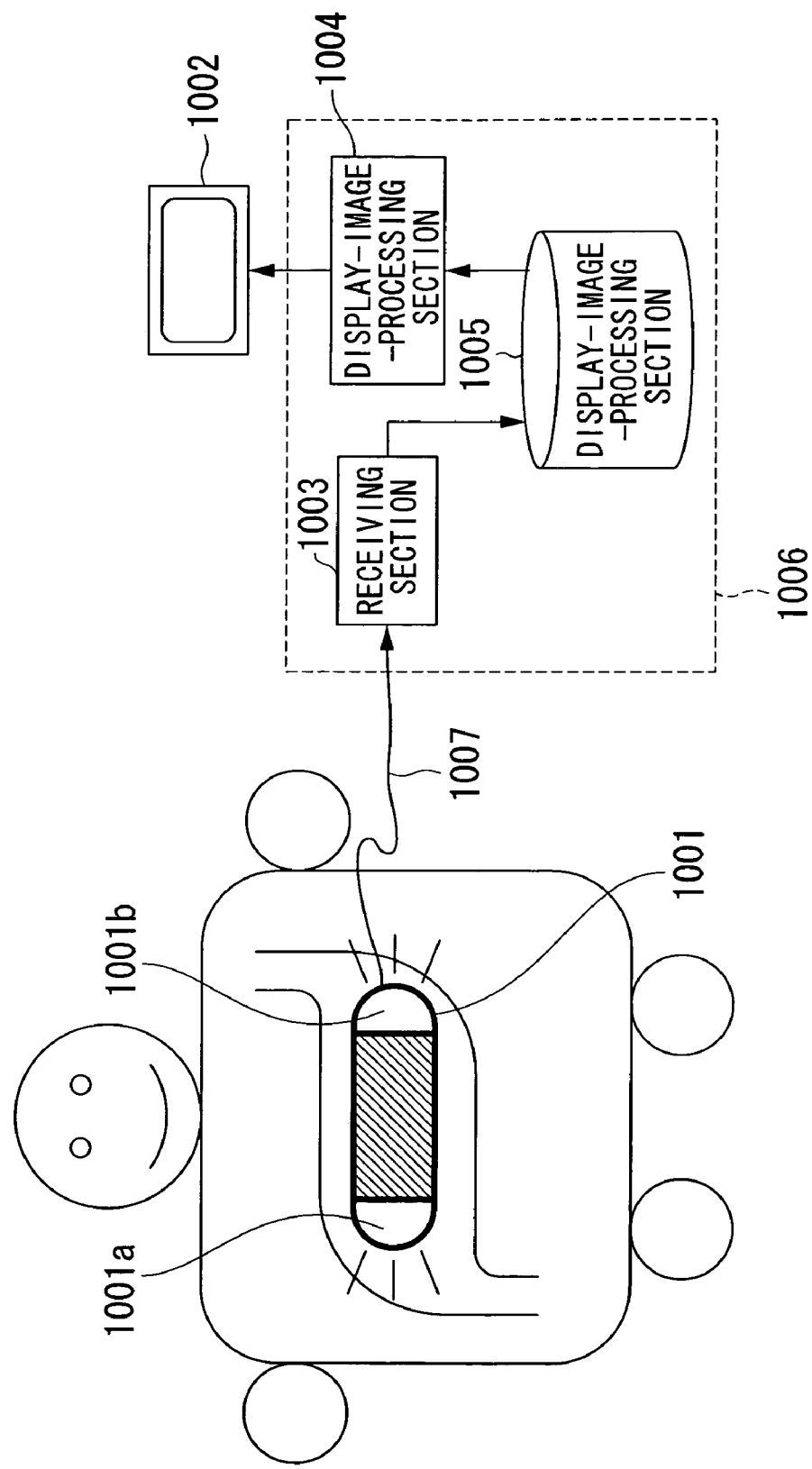
FIG. 10 is a schematic view of an endoscope system according to a second embodiment of the present invention.

Next, a second embodiment of the present invention will be explained. FIG. 10 illustrates the configuration of an endoscope system using an image-pickup apparatus according to the present invention. The endoscope system according to the present embodiment picks up an object image of interior portions of the body of a patient by means of an endoscope (image communication apparatus 1001) swallowed by the patient, and conducts a wireless transmission of the picked up image of the interior portion. The transmitted data is received by a receiving section 1003 in an external device 1006 via a wireless transmission path 1007, and accumulated in an image-accumulating section 1005. The accumulated data subject to display is processed by a displayed-image-processing section 1004, and appears on a monitor 1002.

Preferably, in general cases such as shown in the present embodiment, a wide range object image would be picked up by the swallow-type endoscope. In order to pick up a wider range, the endoscope according to the present embodiment is provided with two image-pickup sections 1001a and 1001b at the front and back of the endoscope.

Figure 11:
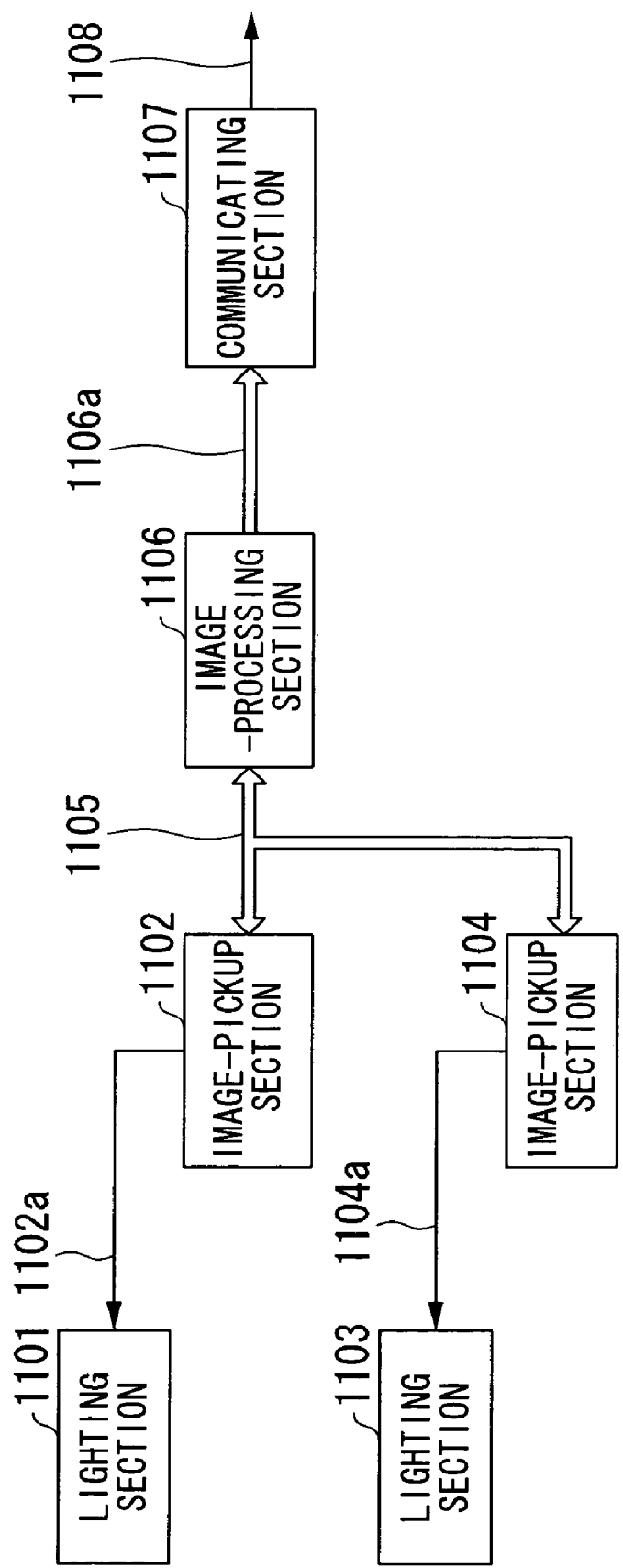
FIG. 11 is a block diagram showing the configuration of an image-communicating device for picking up inner-body image according to the second embodiment of the present invention.

FIG. 11 shows the configuration of an image-communicating device used in an endoscope for picking up an inner-body image according to the present embodiment. The image-communicating device for picking up the inner-body image has: two image-pickup sections 1102 and 1104 (corresponding to the image-pickup sections 1001a and 1001b shown in FIG. 10); lighting sections 1101 and 1103 for lighting an object area to be picked by each image-pickup section; an image-processing section 1106; and a communicating section 1107. Eventually, an image data produced by picking up an object image is output to a transmission path 1108 (corresponding to the transmission path 1007 shown in FIG. 10).

General operations in the image-communicating device for picking up an inner-body image will be explained below with reference to the timing diagram shown in FIG. 12 with respect to the image-communicating device for picking up an inner-body image. In order to save electric power and obtain a sharp object image, a swallow-type endoscope according to the present embodiment flashes light. Flash light pulses 1102a and 1104a, each output from image-pickup sections 1102 and 1104, control the emission of light from lighting sections 1101 and 1103. In the present embodiment, LEDs (light-emitting diodes) are used for the lighting sections 1101 and 1103 because of their small-size and energy-saving advantages. Also, in order to provide optimal lighting of an object to be picked up in the present embodiment, the image-pickup section adjusts light intensity by regulating the duration of the light pulse.

Upon emitting the light, the image-pickup section transmits an image signal (picked-up data). The image signal is input into an image-processing section 1106 via a bus 1105. The image-processing section 1106 conducts various image processes similarly to those in the first embodiment. Since a wireless communication method, having limits in operational bandwidths, is used for transmitting data in the present embodiment, the image-processing section 1106 also compresses an image and outputs the compressed image data to a communicating section 1107. Similarly to the first embodiment, the communicating section 1107 converts the compressed data into a format suitable for data communication and outputs the data to a transmission path 1108.

Preferably, a plurality of successive image-pickup sections must be able to obtain images simultaneously during high speed movement of a swallow-type endoscope depending on an object area. However, since current peak supplied from swallow-type endoscopes using batteries or a wireless power distribution method is limited, circuits thereinside should not be operated simultaneously. In the present embodiment, in order to obtain images as simultaneously as possible but while preventing concurrence of circuit operations, as shown in the timing diagram of FIG. 12, the lighting section 1103 emits light onto an object area to be picked up by the image-pickup section 1104 in synchronization with an end of preceding light emission from the lighting section 1101 for lighting an object area to be picked up by the image-pickup section 1102 so that the emission from the lighting section 1103 is delayed by a predetermined pulse duration.

Operations of the image-pickup sections will be explained below. In the image-pickup sections according to the present embodiment, an optical image formed by an optical system thereinside is converted into an electrical signal by means of an optical sensor (photodiode) thereinside. The electric signal is temporarily stored in a condenser connected to the photodiode. Since objects to be picked up by swallow-type endoscope are internal organs, endoscopes are under dark conditions unless light is emitted, so only an electric charge based on the optical image picked up during the light emission is stored in the condenser. After that, the stored electric signal is amplified by the image-pickup sections and the amplified analogue signal is converted into a digital signal at arbitrary timings. The converted signal, i.e., an image signal, is output therefrom.

Figure 12:
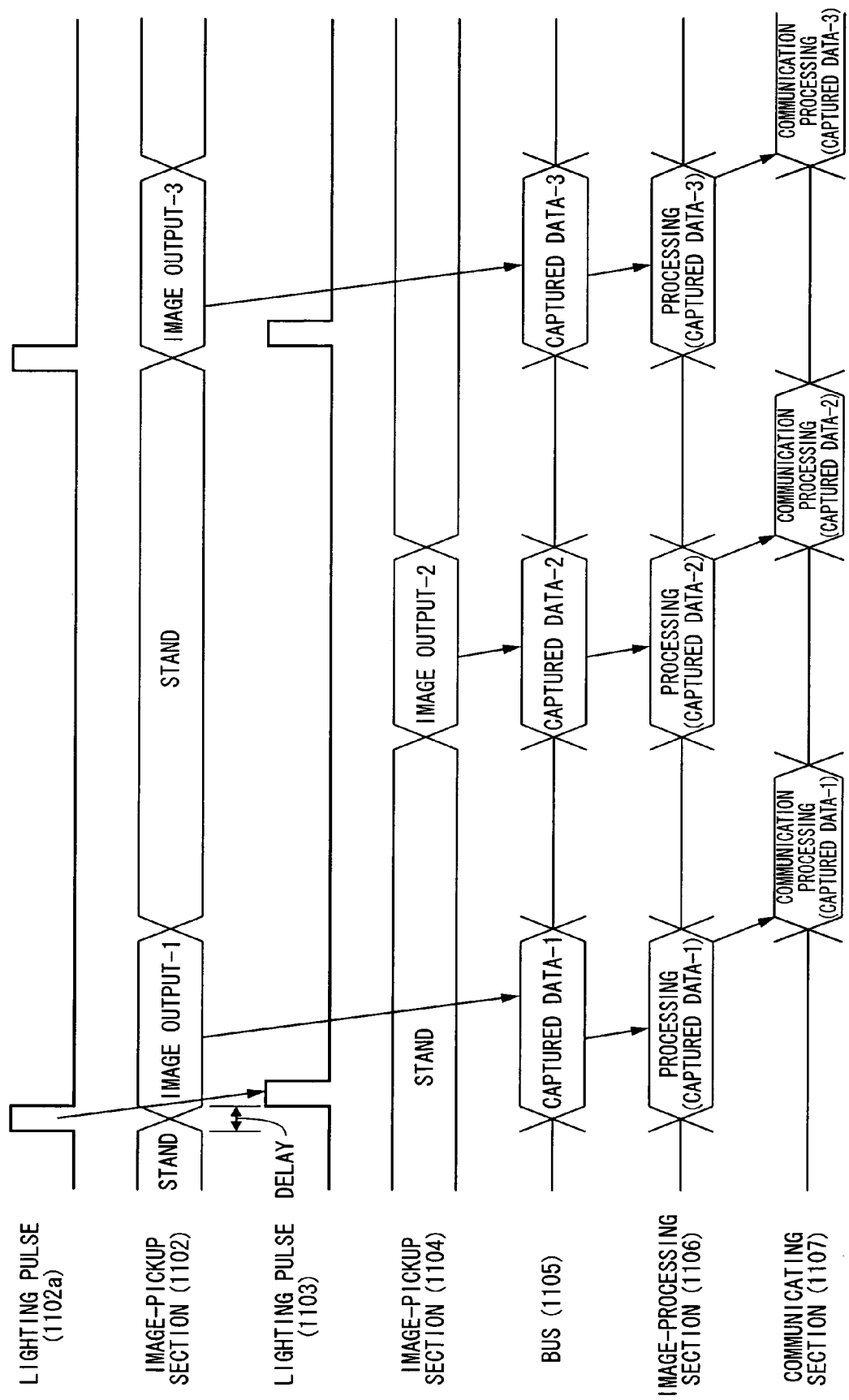
FIG. 12 is a timing diagram showing approximate operation timing of the entire image-communicating device for picking up an inner-body image according to the second embodiment of the present invention.

As shown in FIG. 12, in the present embodiment, the image signal is output from the image-pickup section 1104 to the following image-processing section 1106 after operations in the image-pickup section 1102, the image-processing section 1106, and the communicating section 1107 finish. The details of operations will be hereinafter described. Following the image-pickup section 1102, the image-pickup section 1104 outputs an image signal via a bus 1105 as similarly to the image-pickup section 1102. The image-processing section 1106 conducts image processes, and the communicating section 1107 outputs the image-processed data to the transmission path 1108.

As described above, in the present embodiment, object images each are obtained by extremely slight delay while avoiding concurrent operations by the circuits thereinside.

Figure 13:
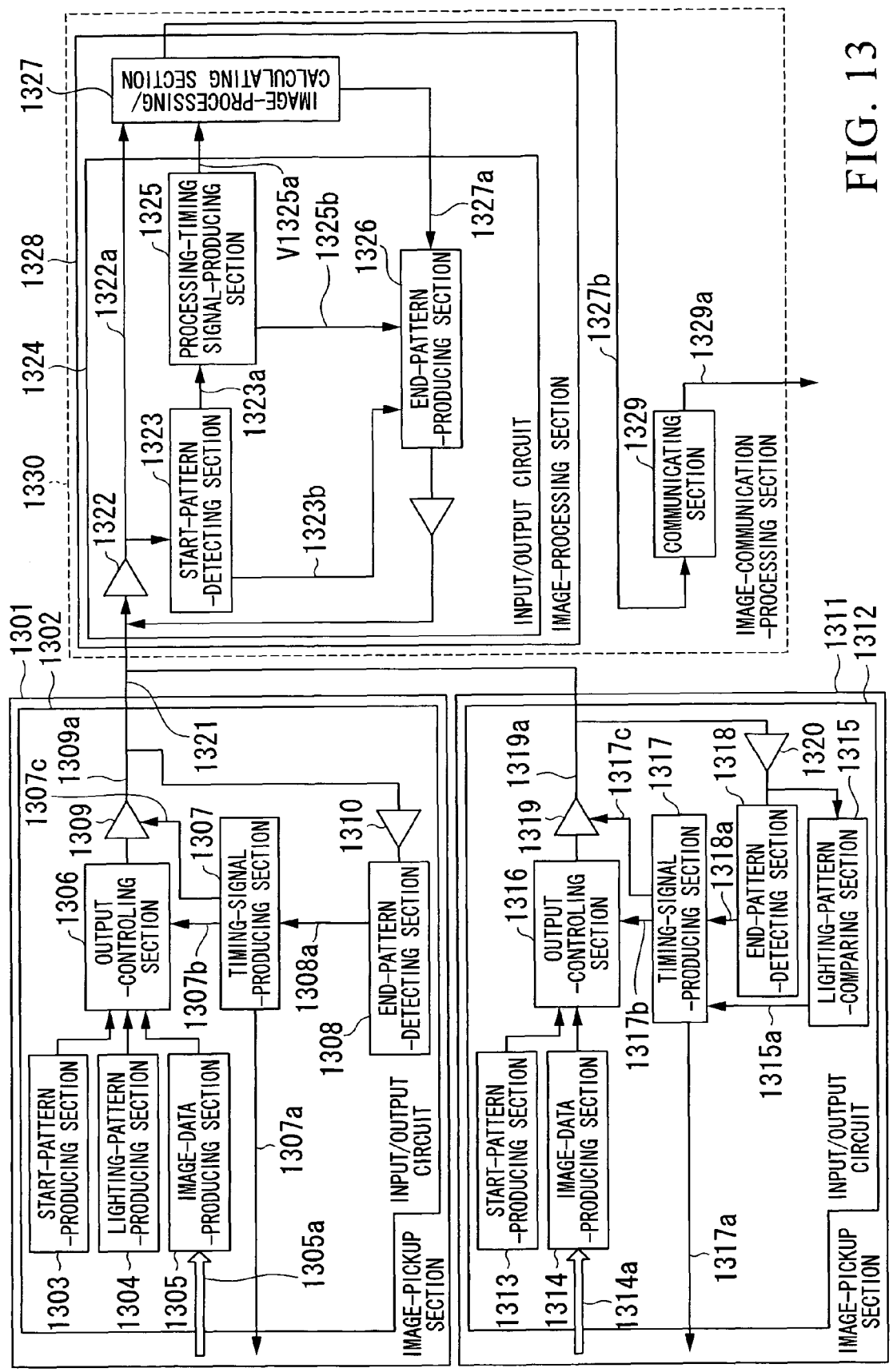
FIG. 13 is a block diagram showing the configuration of the image-communicating device for picking up an inner-body image according to the second embodiment of the present invention.
Figure 14:
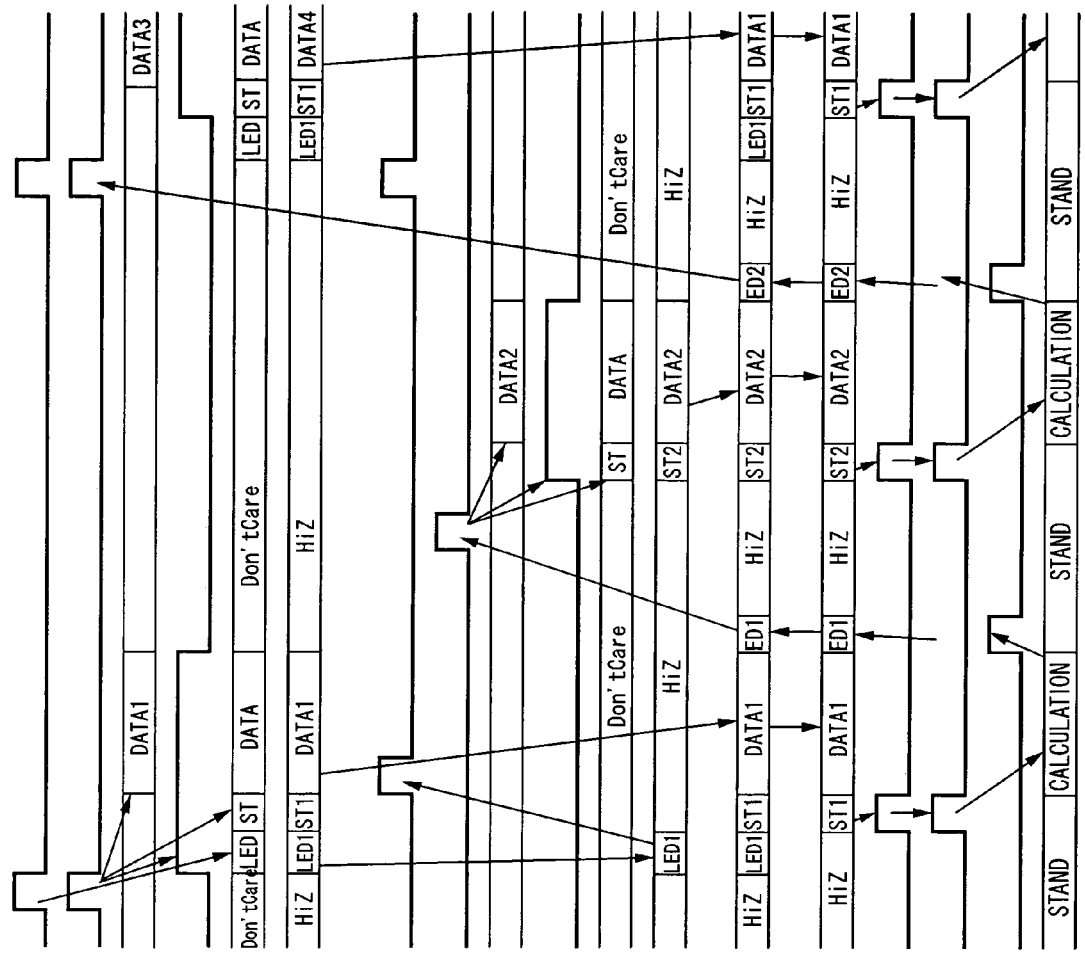
FIG. 14 is a timing diagram showing the operation timing of the image-communicating device for picking up an inner-body image according to the second embodiment of the present invention.

Next, the configurations and operations for realizing the above-described operations will be explained with reference to FIGS. 13 and 14. FIG. 13 shows the configuration in the image-communicating device for picking up an inner-body image. FIG. 14 is a timing diagram of the operations conducted by the image-communicating device for picking up an inner-body image. Upon producing an image-pickup-operation-starting signal 1308a as an internal signal, the image-pickup section 1301 (corresponding to the image-pickup section 1102 shown in FIG. 11) starts the operation. A timing-signal-producing section 1307 produces a light pulse 1307a. The image-pickup section 1301 picks up an image based on this pulse.

Incidentally, a timing-signal-producing section 1307 activates an output-enabling signal 1307c, and outputs an "LED" as a selection signal 1307b which indicates selecting a lighting pattern. An output-controlling section 1306 in the image-pickup section 1301 outputs a lighting pattern "LED1" to a bus 1321 (corresponding to the bus 1105 shown in FIG. 11) via a buffer 1309 in synchronization with the output of the light pulse 1307a. A lighting-pattern-detecting section 1315 in an image-pickup section 1311 (corresponding to the image-pickup section 1104 shown in FIG. 11) monitors the bus 1321, and activates a lighting-timing-signal 1315a upon detecting the lighting pattern "LED1".

Figure 15:
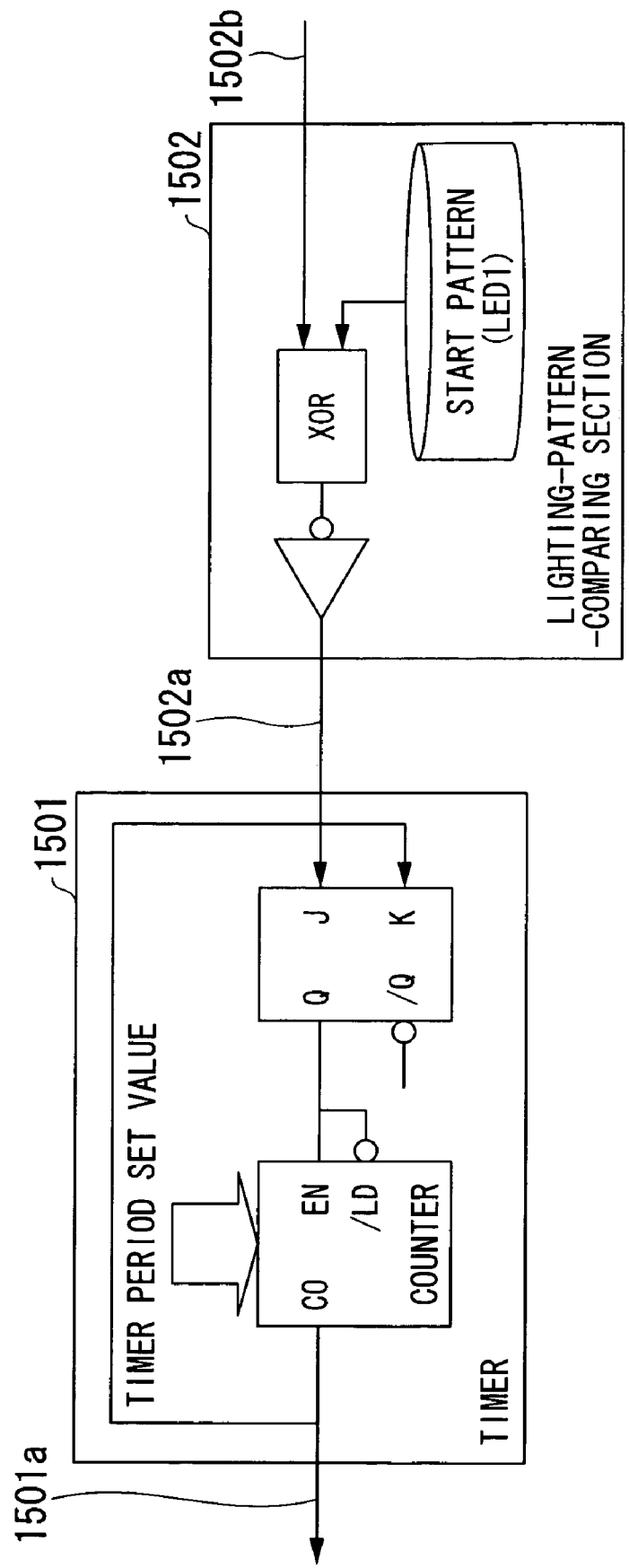
FIG. 15 is a block diagram showing the configuration of a lighting-pattern-detecting section provided in the image-communicating device for picking up an inner-body image according to the second embodiment of the present invention.

FIG. 15 shows the configuration of a lighting-pattern-detecting section 1315. In FIG. 15, a lighting-pattern-comparing section 1502 compares a lighting-pattern-comparing section 1502 with a predetermined lighting pattern. A timer 1501 outputs a lighting-timing-signal 1501a (corresponding to the lighting-timing signal 1315a shown in FIG. 13) after a lapse of predetermined time upon detecting the lighting pattern.

The lighting-pattern-comparing section 1502 compares the predetermined lighting pattern (LED1) with the bus data input 1502b, and if both patterns coincide with each other, the lighting-pattern-comparing section 1502 activates the lighting-pattern-detecting signal 1502a. When the lighting-pattern-detecting signal 1502a becomes active, a counter disposed in a timer 1501 begins incrementing, i.e., taking count of a delay time set by the timer, and after the lapse of a predetermined amount of counted time, the timer 1501 outputs the lighting-timing-signal 1501a. As previously described, it is preferable that emission of light from LEDs and the pick up of an image be as close as possible between the image-pickup section 1301 and the image-pickup section 1311. However, if possible, concurrent light emissions, which may increase the current peak, should be avoided as much as possible. Considering this point, in the present embodiment, the timer 1501 delays the light emission from the image-pickup section 1311 with respect to the light emission from the image-pickup section 1301 by a predetermined time delay.

The configuration and the operation in the image-pickup section 1301 will be explained again with reference to FIGS. 13 and 14. Upon completing the lighting by means of the light pulse 1307a, the timing-signal-producing section 1307 outputs a signal "ST", which corresponds to the selection signal 1307b, for selecting the output of the starting pattern. The output-controlling section 1306 selects the output from the starting-pattern producing section 1303 based on this signal, and outputs a starting pattern "ST1", which indicates the start of outputting data from the image-pickup section 1301, to the bus 1321. After that, the timing-signal-producing section 1307 outputs "DATA", which corresponds to the selection signal 1307b, for selecting the output of data. The output-controlling section 1306 selects the output from the image-data-producing section 1305 based on this signal, and outputs "DATA1" from the image-pickup section 1301 to the bus 1321.

Next, the configurations and the operations in the image-communicating/processing section 1330 will be explained. An image-communicating/processing section 1330 has an image-processing section 1328 (corresponding to the image-processing section 1106 shown in FIG. 11) and a communicating section 1329 (corresponding to the communicating section 1107 shown in FIG. 11). When a starting pattern-detecting section 1323 monitoring the bus 1321 in the image-processing section 1328 detects a starting pattern of data on the bus 1321, the starting pattern-detecting section 1323 outputs a processing-operation-starting-signal 133a. Also, the starting pattern-detecting section 1323 outputs information 1323b of image-pickup section which indicates which one of the image-pickup sections outputs an image data. As shown in FIG. 14, when "ST1", which indicates the start of data from the image-pickup section 1301, is detected by the starting pattern-detecting section 1323, a processing-operation-starting-signal 133a becomes active.

The processing-operation-starting-signal 133a is input into a processing-timing-signal-producing section 1325. The processing-timing-signal-producing section 1325 outputs a timing signal V1325a, which indicates the start of processing operations, to an image-processing/calculating section 1327. Subsequently, the image-processing/calculating section 1327 starts data processes. That is, the image-processing/calculating section 1327 conducts image process and image compression with respect to an image data input from the bus 1321 via the buffer 1322, and after that, the image-processing/calculating section 1327 outputs compressed data 1327b. Also, the image-processing/calculating section 1327 outputs a data size 1327a, which indicates the amount of compressed data 1327b, to an ending-pattern-producing section 1326.

The processing-timing-signal-producing section 1325 produces an ending-pattern-timing signal 1325*b* so as to coincide with an end of the image process. The ending-pattern-producing section 1326 produces an ending pattern "ED1" based on this signal 1325*b*, and outputs the "ED1" to the bus 1321. Incidentally, the ending-pattern-producing section 1326 adds the data size 1327*a* input from the image-processing/calculating section 1327 and the information 1323*b* of image-pickup section input from the starting pattern-detecting section 1323 to the ending pattern, and outputs the resulting ending pattern.

Figure 16:
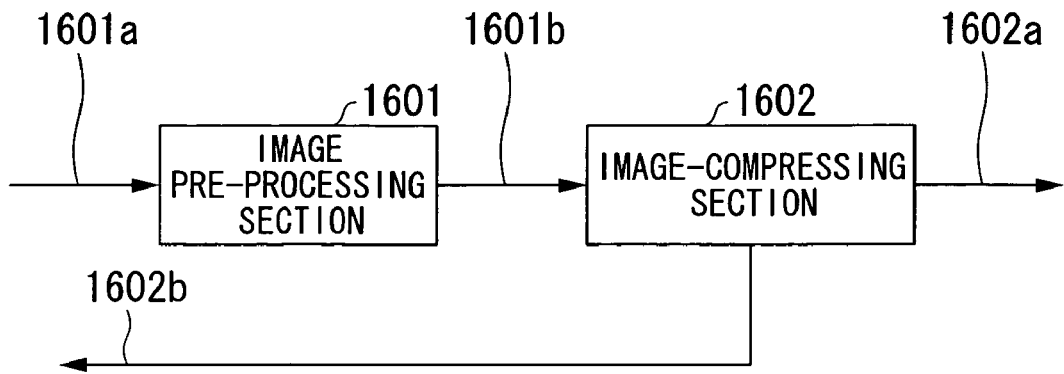
FIG. 16 is a block diagram showing the configuration of an image processing/calculating section provided in the image-communicating device for picking up an inner-body image according to the second embodiment of the present invention.
Figure 17:
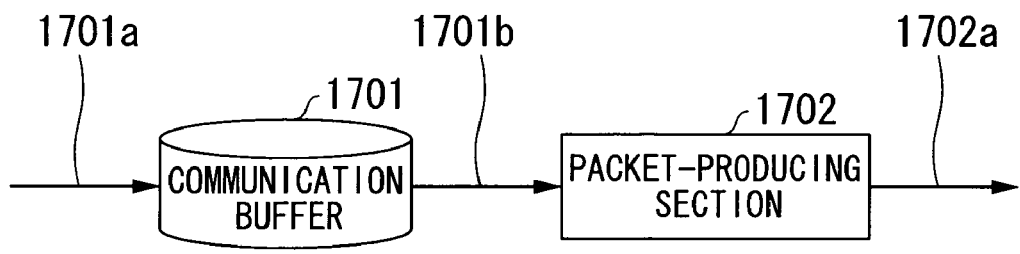
FIG. 17 is a block diagram showing the configuration of a communicating section provided in the image-communicating device for picking up an inner-body image according to the second embodiment of the present invention.
Figure 18:
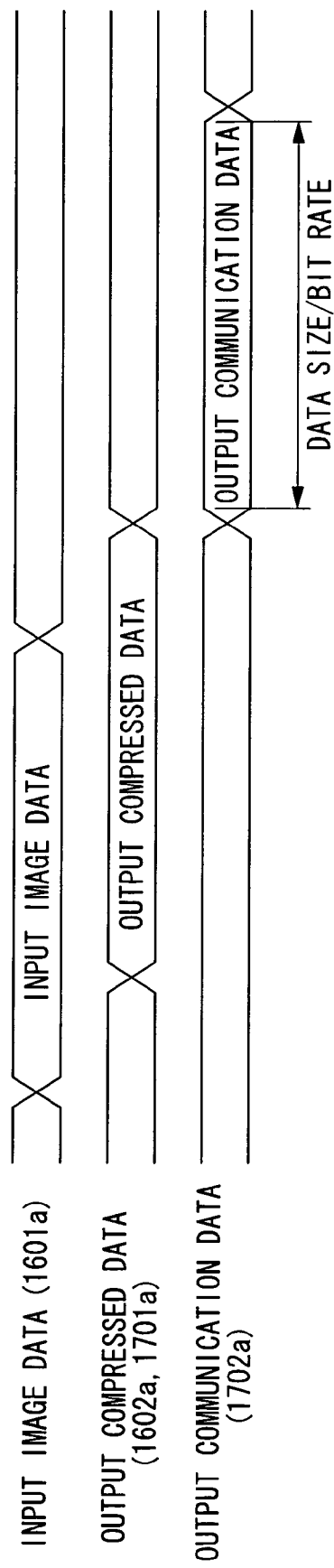
FIG. 18 is a timing diagram showing the operation timing of an image-communicating/processing section provided in the image-communicating device for picking up an inner-body image according to the second embodiment of the present invention.

FIG. 16 shows the configuration of the image-processing/calculating section 1327, FIG. 17 shows the configuration of communicating section 1329, and FIG. 18 is the timing diagram with respect to the image-communicating/processing section 1330. The image-processing/calculating section 1327 has an image-preprocessing section 1601 and an image-compressing section 1602. The image-preprocessing section 1601 conducts various image-preprocesses, e.g., gamma compensation, white-balance adjustment, and color space conversion, so as to optimize the input image data 1601*a* with respect to data compression. The image-compressing section 1602 compresses the processed image 1601*b*, output from the image-preprocessing section 1601, into JPEG format so as to make use of wireless communication bandwidth, and outputs compressed data 1602*a* (corresponding to the compressed data 1327*b* shown in FIG. 13) to a communicating section 1329 disposed thereafter. Also, the image-compressing section 1602 outputs a data size 1602*b* of the compressed data 1602*a*, which is output to the communicating section 1329, to the ending-pattern-producing section 1326.

The communicating section 1329 stores compressed data 1701*a* output from the image-processing/calculating section 1327 (corresponding to the compressed data 1602*a* shown in FIG. 16) in a communication buffer 1701 temporarily, and after that the communicating section 1329 conducts a predetermined conversion in a packet-producing section 1702, i.e., conversion using the 8-10 method and adding an error-correcting redundant-code conversion, and outputs an output communication data 1702*a* (corresponding to the communication data 1329*a* shown in FIG. 13). The compressed data 1602*a* (1701*a*), output from the image-processing/calculating section 1327, is stored in a communication buffer 1701 in the communicating section 1329 temporarily. After that, a packet of data for communication use is produced from buffer data 1701*b* output from the communication buffer 1701 by a packet-producing section 1702, and the packet data is output as an output communication data 1702*a*. In the present embodiment, the output communication data 1702*a* is in 1-bit digital format because the wireless communication is subject to a single channel.

In the present embodiment, bit rate of the transmission path is fixed. As shown in the timing diagram of FIG. 18, the time for outputting the output communication data 1702*a* is indicated by data size/bit rate used in a communication. According to JPEG format used for the data compression in the present embodiment, the time for outputting communication data varies depending on the condition of an image.

As described previously, since the power supply obtainable from the swallow-type endoscope according to the present embodiment is limited, concurrent operations of circuits should preferably be avoided. Therefore, as shown in FIG. 13, the ending-pattern-producing section 1326 in the image-processing section 1328 adds the data size 1327*a*, which indicates information relating to communication time corresponding to time between an end of image process and the start of image-pickup after the image process, to the ending pattern, and transmits it. Also, the ending-pattern-detecting sections 1308 and 1318 in the image-pickup sections 1301 and 1311 detect the ending pattern as well as the communication time and delay the image-pickup operations accordingly so as to prevent concurrence with the communicating section 1329. Since the bit rate is fixed, data size of compressed data is in proportion to the post-image-process communication time, the communication time can be determined based on the data size.

Figure 19:
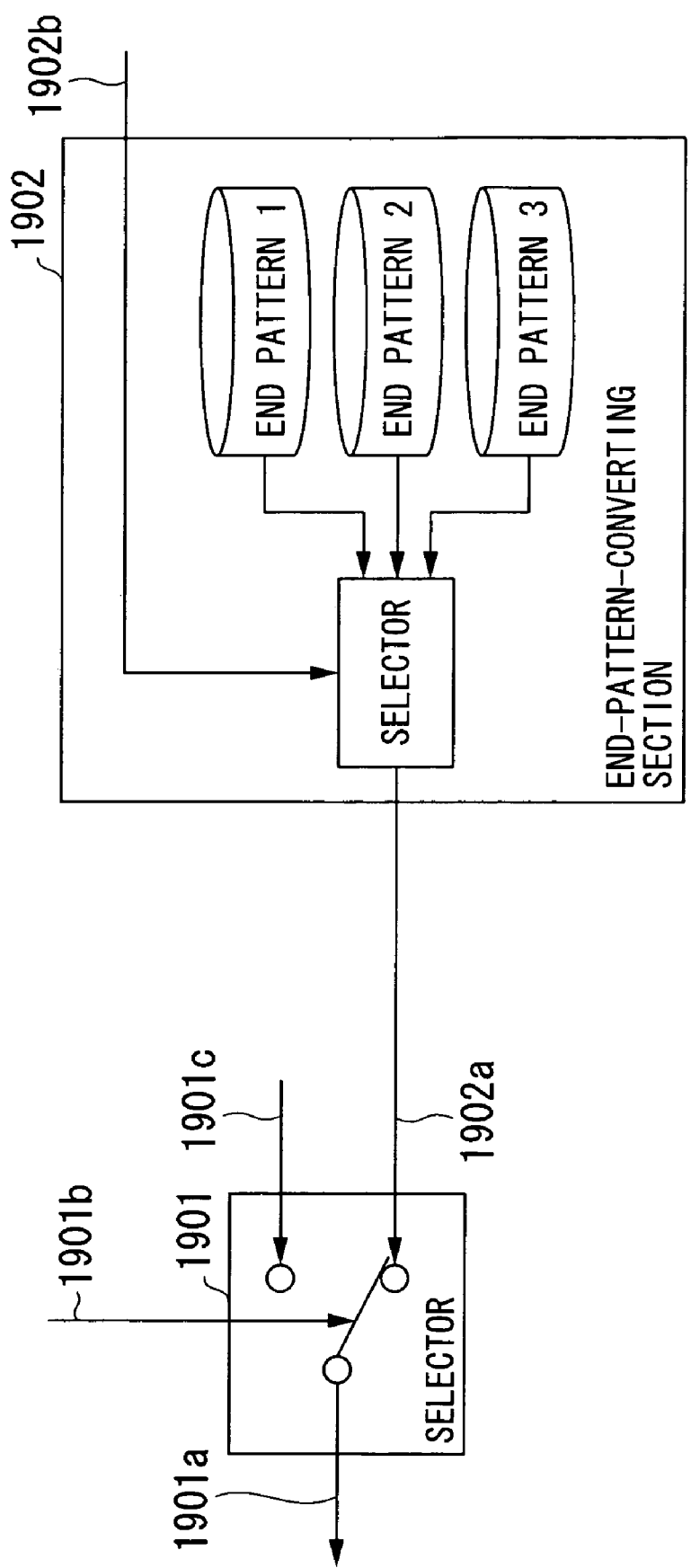
FIG. 19 is a block diagram showing the configuration of an ending-pattern-producing section provided in the image-communicating device for picking up an inner-body image according to the second embodiment of the present invention.

Next, details of the ending-pattern-producing section 1326 in the image-processing section 1328 will be explained. FIG. 19 shows the configuration of the ending-pattern-producing section 1326. As described previously, in the ending-pattern-producing section 1326, an ending-pattern-converting section 1902 selects an ending pattern (ending patterns 1 to 3) which corresponds to the image-pickup section subject to move sequentially, based on the information 1902*b* of image-pickup section which indicates the image-pickup section outputting image data; and thus, the selected pattern is output. A selector 1901 switches among the output of the ending pattern 1902*a*, data size 1901*c*, and OPEN (in HiZ state) based on the end-pattern-timing signal 1901*b* input from the processing-timing-signal-producing section 1325.

Figure 20:
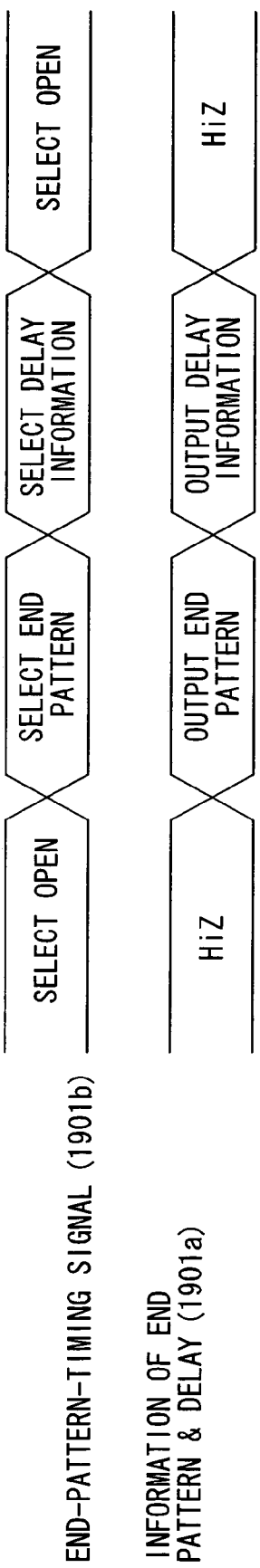
FIG. 20 is a timing diagram showing operation timing of the ending-pattern-producing section provided in the image-communicating device for picking up an inner-body image according to the second embodiment of the present invention.

FIG. 20 shows the timing diagram of the ending-pattern-producing section 1326. When the end-pattern-timing signal 1901*b* output from the processing-timing-signal-producing section 1325 shown in FIG. 13 varies in such an order of SELECT OPEN→select end pattern→select data size→select open after the image process, the state of the ending-pattern-and-delay-information output 1901*a* output from the ending-pattern-producing section 1326 switches from HiZ to the end pattern. Following that, the output 1901*a* varies into a state of delay information having the corresponding data size.

Figure 21:
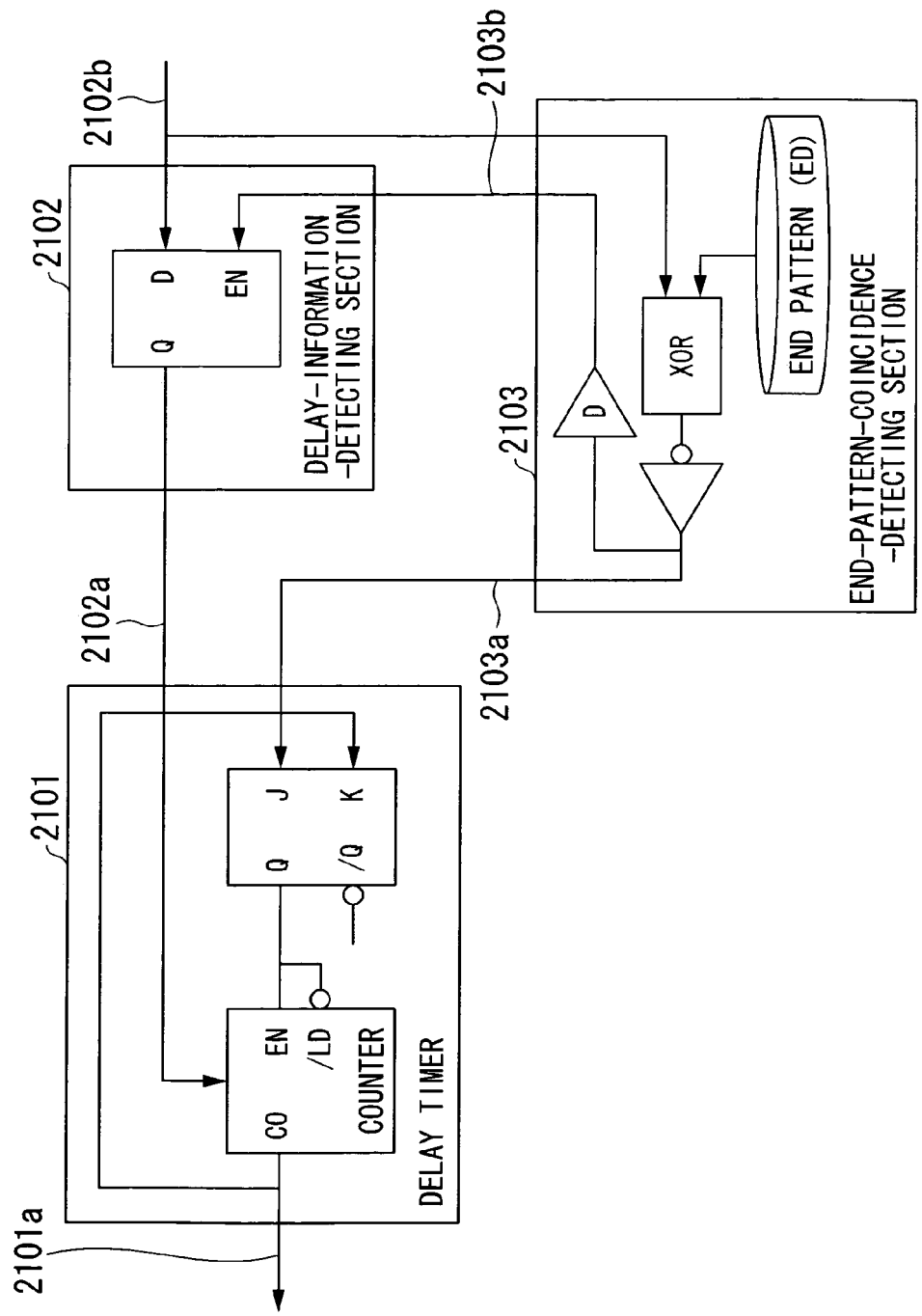
FIG. 21 is a block diagram showing the configuration of an ending-pattern-detecting section provided in the image-communicating device for picking up inner-body image according to the second embodiment of the present invention.
Figure 22:
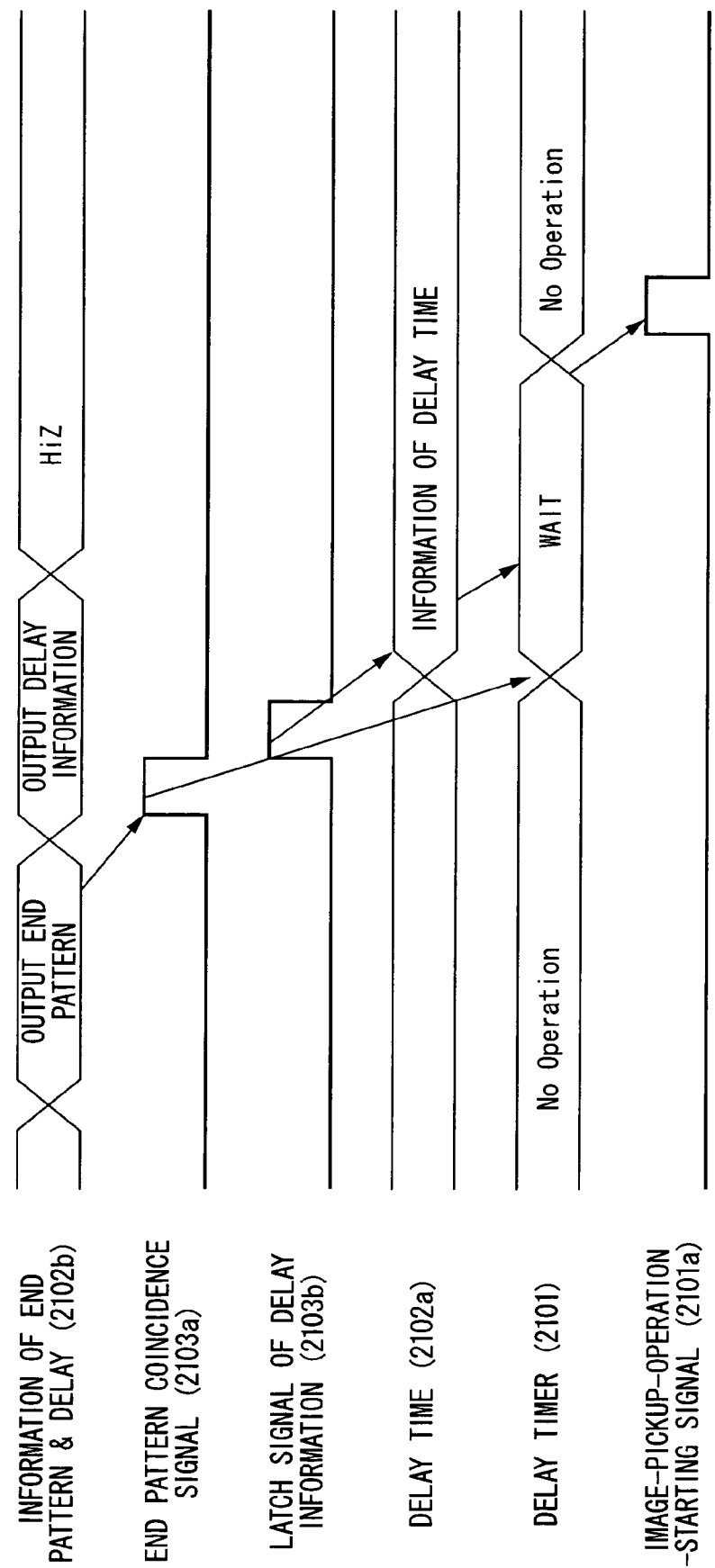
FIG. 22 is a timing diagram showing operation timing of the ending-pattern-detecting section provided in the image-communicating device for picking up an inner-body image according to the second embodiment of the present invention.
Figure 23:
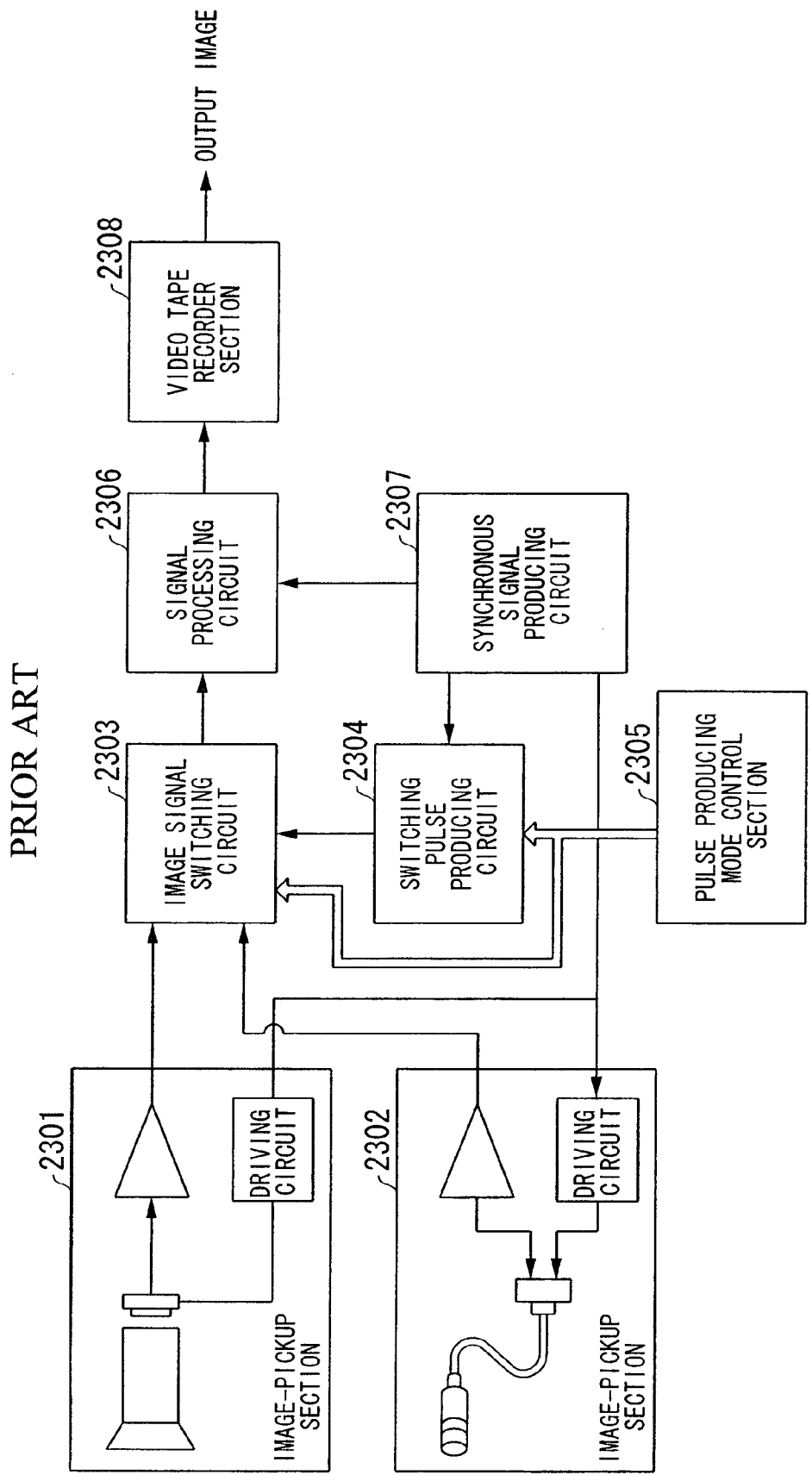
FIG. 23 is a block diagram showing the configuration of a conventional system having a plurality of image-pickup sections.

Next, details of the ending-pattern-detecting sections 1308 and 1318 each provided in the image-pickup section will be explained. FIG. 21 shows the configuration of ending-pattern-detecting sections 1308 and 1318, and FIG. 22 shows the timing diagram thereof. An ending-pattern-coincidence-detecting section 2103 detects an ending pattern from a bus data input 2102*b*, and outputs a coinciding-ending-pattern signal 2103*a* and a delay-information-latching signal 2103*b*. The coinciding-ending-pattern signal 2103*a* indicates that the bus data input 2102*b* coincides with an ending pattern, and the delay-information-latching signal 2103*b* indicates that a previously-described delay information, relating to the data size of compressed data following the ending pattern, is detected.

The delay-information-detecting section 2102 latches the delay information from the bus data input 2102*b* in accordance with the delay-information-latching signal 2103*b*, and outputs an initial-setting-delay-period value 2102*a*. The initial-setting-delay-period value 2102*a* and the coinciding-ending-pattern signal 2103*a* are input into a delay timer 2101. The delay timer 2101 takes count of stand-by time corresponding to the delay time after a coinciding-ending-pattern signal 2103*a* becomes active, and after that, the delay timer 2101 outputs an image-pickup-operation-starting signal 2101*a* for controlling the timing of starting the image-pickup operation. The time delayed by the delay timer 2101 based on the data size of compressed data corresponds to the communication time of a communicating section 1329 since the frequency of operation conducted by the counter in the delay timer 2101 corresponds to the bit rate of transmission path. Accordingly, each image-pickup section starts an image pickup operation sequentially based on the end of operations in the communicating section 1329 disposed posterior thereto.

The timing diagram will be explained again with reference to FIG. 14. When the image-processing section 1328 outputs an ending pattern "ED1", having the delay information (data size), to the bus 1321, the ending-pattern-detecting section 1318 in the image-pickup section 1311 detects an ending pattern, and after a predetermined lapse of time, the ending-pattern-detecting section 1318 outputs the image-pickup-operation-starting signal 1318a. Consequently, the image-pickup section 1311 starts transferring images sequentially similar to the image-pickup section 1301.

As described previously, the light pulse 1317a in the image-pickup section 1311 is in synchronization with the light pulse 1307a in the image-pickup section 1301. An image obtained when a light is emitted based on the light pulse 1317a is accumulated in an optical sensor. The accumulated image is retrieved from the optical sensor synchronously with the image-pickup-operation-starting signal 1318a and transmitted. Upon completing the output of the data, the image-processing section 1328 outputs an image-processing-ending pattern "ED2", which indicates the end of processing an image data obtained from the image-pickup section 1311, to the bus 1321. Following that, the ending-pattern-detecting section 1308 in the image-pickup section 1301 detects an ending pattern and produces an image-pickup-operation-starting signal 1308a again; thus, the image-pickup section 1301 starts sequential operations similarly to the image-pickup section 1311.

As described previously, each image-pickup section and the image-processing section are connected by a single bus in the image-pickup apparatus according to the present embodiment, and prior to the start of outputting image data, each image-pickup section outputs a specific starting pattern produced in the starting pattern-producing section. Also, the image-processing section detects a starting pattern on a bus by means of the starting pattern-detecting section, and starts the image-processing operation. Upon completing the input of image data and the image processing operation, the ending-pattern-producing section in the image-processing section outputs an ending pattern corresponding to an image-pickup section subject to operate sequentially. By doing this, the sequential image-pickup operation can be conducted in each image-pickup section, and the sequential image-processing operation can be conducted in the image-processing section without providing a specific signal line for controlling the operation.

The ending-pattern-producing section in the image-processing section adds delay information, which indicates the time for delaying a subsequent image-pickup operation, to an ending pattern, and outputs the information to a bus. The ending-pattern-detecting section in the image-pickup section detects the ending pattern and the delay information on the bus, and delays a signal for starting an image-pickup operation after a predetermined lapse of time after detecting the ending pattern in proportion with the delay information; thus, the delayed signal is output therefrom. Accordingly, the communicating section and each image-pickup section can be controlled exclusively without providing a signal line between each image-pickup section and the image-processing section.

The lighting-pattern-producing section and the output-controlling section in the first image-pickup section output lighting patterns to the bus in synchronization with the light pulses. The lighting-pattern-detecting section in the second image-pickup section detects a lighting pattern on the bus, and the timing-signal-producing section produces a lighting pulse in synchronization therewith. By doing this, only lighting moments can be synchronized among the plurality of image-pickup sections without providing a controlling-signal line in each image-pickup section.

Therefore, according to the present embodiment, an increase in peak current can be restrained, and object images can be obtained at substantially the same moment by the image-pickup sections while operating two image-pickup sections exclusively. Although the present embodiment provides an example using two image-pickup sections, a different number of similarly-configured image-pickup sections, i.e., three or more image-pickup sections similar to the case of first embodiment can be realized in the present invention.

The embodiments of the present invention have been explained above in detail with reference to the drawings. However, it should be understood that the drawings and detailed description thereto are not intended to limit the invention to the particular form disclosed; thus, the invention disclosed herein is susceptible to various modifications and alternative forms, i.e., design changes. For instance, the method for setting the initial-setting values in each image-pickup section in the communicating device of monitoring camera according to the first embodiment may be applied to the image-communicating device for picking up an inner-body image according to the second embodiment. Also, in a system having a plurality of image-pickup sections, if at least two image-pickup sections and an image-processing section are connected via a single bus and the system can provide a common function similar to the above described embodiments, such a system is within a scope of the present invention.

According to the present invention, effects can be obtained that the number of signal lines for connecting each image-pickup section and the image-processing section can be reduced, and the circuit configuration may be simpler since each image-pickup section and an image-processing section are connected by a single bus.

What is claimed is:
1. An image-pickup apparatus comprising:
   a plurality of image-pickup units including at least first and second image-pickup units each for picking up an image, producing and outputting image data;
   an image-processing unit for performing a predetermined data process on the image data; and
   a bus for connecting the first and second image-pickup units to the image-processing unit, wherein
   the first image-pickup unit has an image-data-ending-pattern-outputting unit for outputting an image-data-ending pattern, which indicates the end of outputting the image data, to the bus, and an image-data-starting-pattern-outputting unit for outputting an image-data-starting pattern, which indicates the start of outputting the image data, to the bus,
   the second image-pickup unit has an image-data-processing-ending-pattern-detecting unit for detecting the image-data-ending pattern output from the first image-pickup unit so that pick up of the image and output the image data start when the image-data-ending pattern is detected by the image-data-processing-ending-pattern-detecting unit, and the image-processing unit further has an image-data-starting-pattern-detecting unit for detecting the image-data-starting pattern output from the first image-pickup unit, so that the data process starts when the image-data-starting pattern is detected by the image-data-staring-pattern-detecting unit.

2. An image-pickup apparatus comprising:
a plurality of image-pickup units including at least first and second image-pickup units each for picking up an image, and producing and outputting image data;
an image-processing unit for performing a predetermined data process on the image data; and
a bus for connecting the first and second image-pickup units to the image-processing unit, wherein
the first image-pickup unit further has an image-data-starting-pattern-outputting unit for outputting an image-data-starting pattern, which indicates the start of outputting the image data, to the bus,
the image-processing unit further has:
an image-data-starting-pattern-detecting unit for detecting the image-data-starting pattern output from the first image-pickup unit; and
an image-processing-ending-pattern outputting unit for outputting the image-processing-ending pattern, which indicates the end of the data process, to the bus in synchronization with the timing of ending the data process,
the second image-pickup unit further has the image-data-processing-ending-pattern-detecting unit for detecting an image-processing-ending pattern from the bus,
the second image-pickup unit starts the pickup of an image and outputting of the image data when the image-processing-ending pattern is detected by the image-data-processing-ending-pattern-detecting unit, and
the image-processing unit starts processing the image data when the image-data-starting pattern is detected by the image-data-starting-pattern-detecting unit.

3. An image-pickup apparatus according to claim 2, wherein
the image-processing unit further has a delay-information-adding unit for adding delay information, which relates to an interval between the end of data process and the start of pick up of an image, to the image-processing-ending pattern, and
the second image-pickup unit further has a unit for controlling the timing of starting the picking up of an image, the unit controlling the timing of starting the pick up of an image based on the delay information added to the image-processing-ending pattern so that the pick up of the image starts after a lapse of time based on the delay information.

4. An image-pickup apparatus according to claim 2, further comprising:
a first lighting unit for lighting an object area picked up by the first image-pickup unit; and
a second lighting unit for lighting an object area picked up by the second image-pickup unit, wherein
the first image-pickup unit further has:

a first lighting-signal-producing unit for producing a first lighting signal for driving the first lighting unit; and
a synchronous-lighting-pattern-outputting unit for outputting a synchronous lighting pattern onto the bus corresponding to the first lighting signal, and
the second image-pickup unit further has:
a synchronous-lighting-pattern-detecting unit for detecting the synchronous lighting pattern on the bus; and
a second lighting-signal-producing unit for producing a second lighting signal for driving the second lighting unit when the synchronous lighting pattern is detected by the synchronous-lighting-pattern-detecting unit.

5. An image-pickup apparatus according to claim 2, wherein the first image-pickup unit further has:
an initial-setting-starting-pattern-outputting unit for outputting an initial-setting starting pattern, which indicates the start of outputting an initial-setting data, to the bus; and
an initial-setting-data-outputting unit for outputting the initial-setting data to the bus after outputting the initial-setting-starting pattern, and
the second image-pickup unit further has:
an initial-setting-data-storing unit for storing the initial-setting data;
an initial-setting-starting-pattern-detecting unit for detecting the initial-setting-starting pattern on the bus; and
an initial-setting-data-receiving unit for receiving the initial-setting data on the bus when the initial-setting-starting pattern is detected by the initial-setting-starting-pattern-detecting unit, the initial-setting-data-receiving unit storing the received initial-setting data in the initial-setting-data-storing unit.

6. An image-pickup apparatus according to claim 2, wherein the second image-pickup unit further has:
an initial-setting-starting-pattern-outputting unit for outputting a initial-setting starting pattern, which indicates the start of outputting initial-setting data, to the bus, the initial-setting data relating to a setting of operation modes of the first image-pickup unit; and
an initial-setting-data-outputting unit for outputting the initial-setting data to the bus after outputting the initial-setting-starting pattern, and
the first image-pickup unit further has:
an initial-setting-data-storing unit for storing the initial-setting data;
an initial-setting-starting-pattern-detecting unit for detecting the initial-setting-starting pattern on the bus; and
an initial-setting-data-receiving unit for receiving the initial-setting data on the bus when the initial-setting-starting pattern is detected by the initial-setting-starting-pattern-detecting unit, the initial-setting-data-receiving unit storing the received initial-setting data in the initial-setting-data-storing unit.

* * * * *